(12) United States Patent
Glover, Sr.

(10) Patent No.: US 11,568,994 B2
(45) Date of Patent: Jan. 31, 2023

(54) SMART TOILET SYSTEM

(71) Applicant: Russell Sebastian Glover, Sr., Boston, MA (US)

(72) Inventor: Russell Sebastian Glover, Sr., Boston, MA (US)

( * ) Notice: Subject to any disclaimer, the term of this patent is extended or adjusted under 35 U.S.C. 154(b) by 0 days.

(21) Appl. No.: 17/335,043

(22) Filed: May 31, 2021

(65) Prior Publication Data

US 2021/0375470 A1     Dec. 2, 2021

Related U.S. Application Data

(60) Provisional application No. 63/031,972, filed on May 29, 2020.

(51) Int. Cl.
| | | |
|---|---|---|
| *G16H 50/00* | (2018.01) | |
| *G16H 50/30* | (2018.01) | |
| *G16H 40/67* | (2018.01) | |
| *A47K 13/28* | (2006.01) | |
| *A47K 13/10* | (2006.01) | |
| *G16H 50/20* | (2018.01) | |

(52) U.S. Cl.
CPC .......... *G16H 50/30* (2018.01); *A47K 13/105* (2013.01); *A47K 13/28* (2013.01); *G16H 40/67* (2018.01); *G16H 50/20* (2018.01)

(58) Field of Classification Search
CPC .... A47K 13/105; A47K 13/28; A47K 13/302; G16H 40/67; G16H 50/30; G16H 50/20
See application file for complete search history.

(56) References Cited

U.S. PATENT DOCUMENTS

| | | | |
|---|---|---|---|
| 2002/0035749 A1* | 3/2002 | Prisco | E03D 9/05 4/213 |
| 2011/0099700 A1* | 5/2011 | Seibt | B64D 11/02 4/249 |
| 2014/0059750 A1* | 3/2014 | Bochnik | E03D 9/052 4/213 |
| 2016/0338556 A1* | 11/2016 | Payziev | A47K 13/307 |
| 2017/0073952 A1* | 3/2017 | Slover | E03D 9/05 |
| 2018/0303466 A1* | 10/2018 | Kashyap | A61B 10/007 |
| 2019/0369085 A1* | 12/2019 | Tan | E03D 9/00 |
| 2020/0393442 A1* | 12/2020 | Hall | G01N 33/493 |

FOREIGN PATENT DOCUMENTS

CN     211472756 U  *  9/2020

* cited by examiner

*Primary Examiner* — Jennifer Pitrak McDonald
*Assistant Examiner* — Sana Sahand

(57) ABSTRACT

Improved toilet apparatus and accessories are provided. The smart toilet system comprises components to enhance the functionality and use of existing toilets or new toilets. The smart toilet system comprises components designed to be fit in, on, above, or under a toilet seat, or to replace a toilet seat, bidet components, health monitoring components, ventilation or hygiene components, and communications and/or control components.

20 Claims, 32 Drawing Sheets

SMART TOILET SYSTEM

CROSS-REFERENCE TO RELATED APPLICATION

This application claims priority to U.S. provisional patent application 63/031,972, titled "Smart Toilet System", and filed 2020 May 29, by Russell Sebastian Glover, Sr.

FIELD OF THE INVENTION

The present disclosure relates to accessories and improvements for plumbing fixtures including but not limited to toilets, and more specifically, to components designed to be fit on, above, or under a toilet seat, or to replace a toilet seat, bidet components, health assistive and health monitoring components, ventilation or hygiene components, and communications and/or control components to accompany toilets.

BACKGROUND OF THE INVENTION

For many people with physical ailments, certain routine health-related tasks can be important or even essential for maintaining the stability of their health. Some of these tasks can include odor removal, wiping, IR light treatment, and measuring blood pressure, glucose monitor, weight, body mass index ("BMI"), smart optical sensor waste analyzer, intense pulse light for perineum and anus hair removal, and body percentages and temperature. However, due to physical limitations, these actions may be challenging or not plausible at all. Toilets are used by a majority of the population, regardless of the health of a person. Introducing certain routine healthcare functions into toilet systems with automatic functionalities can provide an easier means for those who need health care monitoring and self-care but face challenges in doing so. Prior art devices exist, such as U.S. Pat. No. 10,292,658 to Borkholder et al., for a system and method for measurement and analysis of a seated individual, as may be used in a toilet seat, and U.S. Pat. No. 4,800,973 to Angel for a thin electronic scale. However, none of the foregoing present the many advantages and capabilities of the present disclosure.

For these reasons, a need exists for a smart toilet system that provides health functionalities, measurements, data tracking, and assistance with human hygiene.

SUMMARY OF THE INVENTION

The present invention meets all these needs, by disclosing apparatus for odor removal, wiping, IR light treatment, and measuring blood pressure, glucose levels, weight, body mass index ("BMI"), body fat percentages, and temperature, in an apparatus comprising a smart optical sensor waste analyzer, an intense pulse light for perineum and anus hair removal, and more. The embodiments of the invention described herein relate to a smart toilet system having the capability of performing routine health-related tasks, routine hygiene-related functions, and certain toilet functions. The smart toilet system includes a control box, an ORG, (Odor Removal Gasket), that houses a secondary control center, a wiper system for toilet users with two bidet sprayer heads and one or more sensing devices. The input signal from the one or more sensors, ideally from each sensor separately, is directed to a processor, whereby the processor interprets the input and initiates one or more control actions, such as, but not limited to, flushing, wiping, hair removal, infrared light therapy, causing certain data points and biomarkers such as weight, BMI, blood pressure, body temperature or other similar information to be captured and reported, activating odor control systems, activating lighting elements, activating electronics such as displays or speakers, and other electronics devices, based on the input, in conjunction with the control box. For example, the processing circuit will receive a signal from a sensor and determine, based on the signal, an action or task to be performed. More specifically, the processing circuit will receive a signal from a motion sensor and determine, based on the signal, that a user is present. The processing circuit may cause lights supported by the smart toilet system to turn on when the user is present. As will be described and shown herein the control center may support various other electronical, mechanical, and plumbing components.

In one aspect, the present invention comprises a smart toilet system, the smart toilet system comprising: a toilet seat; a toilet seat cover; and an ORG comprising a body, the ORG having hollow regions within the body of the ORG; and the ORG comprises a plurality of front odor openings and a plurality of rear odor openings; and the ORG comprises a front end; and the ORG comprises a housing, and wherein the housing comprises a top surface, a bottom surface, and a plurality of side surfaces; and wherein the front end of the ORG is located on the toilet seat, or is affixed to the toilet seat, or is affixed to a toilet bowl.

In one aspect, the present invention comprises a smart toilet system, in which the ORG comprises a vacuuming system and a processor and a processing circuit.

In one aspect, the present invention comprises a smart toilet system, in which the ORG further comprises a processor, and the ORG further comprises an ORG processing-unit, and in which the ORG houses or supports a plurality of motion sensors, a plurality of lighting elements, a plurality of body weight sensors, a plurality of impedance photoplethysmography sensors, a glucose monitor, and/or a plurality of infrared lights, collectively a plurality of sensors, and wherein the plurality of sensors are in electrical communication with the ORG-processing-unit, and wherein the ORG-processing-unit communicates a plurality of data and input received from the ORG and the plurality of sensors to the processor.

In one aspect, the present invention comprises a smart toilet system, in which any of the lighting elements, the body weight sensors, the infrared lights, or the impedance photoplethysmography sensors may be activated or de-activated based on an input to at least one of the one or more of the motions sensors.

In one aspect, the present invention comprises a smart toilet system, in which a plurality of the plurality of motion sensors is located at a plurality of tips of the ORG.

In one aspect, the present invention comprises a smart toilet system, in which the infrared lights may be placed under or on an upper surface of the toilet seat and/or at an inner side of the toilet seat, and the glucose monitor and the impedance photoplethysmography sensors may be disposed on the toilet seat cover.

In one aspect, the present invention comprises a smart toilet system, in which the ORG further comprises an optical sensor waste analyzer, wherein the optical sensor waste analyzer scans and analyzes one or more samples of a user's urine and/or fecal matter for diagnosis or treatment of medical conditions or diseases, including but not limited to COVID-19 and comorbidities for COVID-19.

In one aspect, the present invention comprises a smart toilet system, in which the ORG further comprises a rear bidet sprayer head, a front bidet sprayer head, a user arm controller, a toilet user's wiper system, a plurality of rear odor openings, and an odor removal system through a VET.

In one aspect, the present invention comprises a smart toilet system, in which the user arm controller contains a UAC-processing-unit, which UAC-processing-unit provides input from the user arm controller to an ORG-processing-unit of the ORG.

In one aspect, the present invention comprises a smart toilet system, further comprising one or two heating vessels which is temperature-controlled and/or insulated, and is used to regulate water temperature from a water supply and/or supply fluids (toiletries and medicinal) that is at a comfortable temperature to a rear bidet sprayer head and/or to a front bidet sprayer head.

In one aspect, the present invention comprises a smart toilet system, in which the smart toilet system further comprises a remote control, and wherein the remote control is implemented as one or more software applications used to store, log, track, and/or share information related to diagnosis or treatment of medical conditions or diseases, including but not limited to COVID-19 and comorbidities for COVID-19.

In one aspect, the present invention comprises a smart toilet system, in which the toilet seat further comprises a smooth flush finish, which smooth flush finish may be fitted at the top of the toilet seat or may cover part of the surface of the top of the toilet seat, and wherein the smooth flush finish further comprises a plurality of impedance photoplethysmography sensors, a plurality of infrared lights, a plurality of electrodes, and a plurality of temperature sensors, and a sticker attachment.

In one aspect, the present invention comprises a smart toilet system, in which the plurality of electrodes transmits sound waves from the toilet seat.

In one aspect, the present invention comprises a smart toilet system, in which an intense pulse light is disposed at or approximately at a top and center position of the toilet seat cover.

In one aspect, the present invention comprises a smart toilet system, further comprising one or more of an electronic blood pressure cuff-defibrillator-electrode.

In one aspect, the present invention comprises a smart toilet system, in which the smart toilet system further comprises a fan deodorizer, a vacuuming system, and may comprise a VET providing connection to a bathroom exhaust fan, and in which the smart toilet system removes odor through the ORG whereby the vacuuming system and the rear odor openings remove odor.

In one aspect, the present invention comprises a smart toilet system, in which the smart toilet system further comprises an automatic flush mechanism comprising a toilet handle, and a switch, wherein the switch is attached to a toilet tank, and wherein the switch actuates a rodded handle or a switch for the push down type button on the tank lid.

In one aspect, the present invention comprises a smart toilet system, comprising an ORG and a toilet user's wiper system; wherein the toilet paper wiper system comprises a tissue roll feeder, a toilet-paper-feeder port, a plurality of conveyor belts, a plurality of toilet paper, a pressure plate, a plurality of cylindrical balls, a motorized hygiene wiper, and an extensible arm; and wherein the motorized hygiene wiper may extend the plurality of cylindrical balls out of the ORG and into a space of a toilet bowl below a user, utilizing the extensible arm; and wherein the plurality of conveyor belts contacts the plurality of toilet paper, and the plurality of conveyor belts rotate to wrap one or more layers of toilet paper around the plurality of conveyor belts and around the plurality of cylindrical balls.

In one aspect, the present invention comprises a smart toilet system, which the cylindrical balls are rotated by the motorized hygiene wiper and the extensible arm to effectively wipe the user of waste; after which, the cylindrical balls are rotated down from a horizontal level, whereupon the cylindrical balls are collapsed or reduced in volume; after which the cylindrical balls are rotated back to the horizontal or approximately horizontal, and are retracted by the motorized hygiene wiper and the extensible arm back into the ORG.

A smart toilet system, the smart toilet system comprising: an ORG, wherein the ORG comprises a plurality of front odor openings and a plurality of rear odor openings; a VET comprising a VET arm connector with a sensor; and two other optional attachments are one or more toilets with ORGs or for odor or smoke removal, could be a cat litter box, a handheld smoking device; and wherein the ORG, the VET, and the other optional attachments to be vacuumed are operably interconnected to the vacuuming system; and wherein the vacuuming system is activated or deactivated by sensors, and/or a remote control, and/or motion sensors.

These aspects of the present disclosure, and others disclosed in the Detailed Description of the Drawings, represent improvements on the current art. This summary is provided to introduce a selection of concepts in a simplified form that are further described below in the Detailed Description of the Drawings. This Summary is not intended to identify key features for essential features of the claimed subject matter, nor is it intended to be used to limit the scope of the claimed subject matter.

BRIEF DESCRIPTION OF THE DRAWINGS

The foregoing summary, as well as the following detailed description of various aspects, is better understood when read in conjunction with the appended drawings. For the purposes of illustration, there is shown in the drawing's exemplary aspects; but the presently disclosed subject matter is not limited to the specific methods and instrumentalities disclosed. In the drawings, like reference characters generally refer to the same components or steps of the device throughout the different figures. In the following detailed description, various aspects of the present invention are described with reference to the following drawings, in which.

DETAILED DESCRIPTION OF THE DRAWINGS

Figure 1:
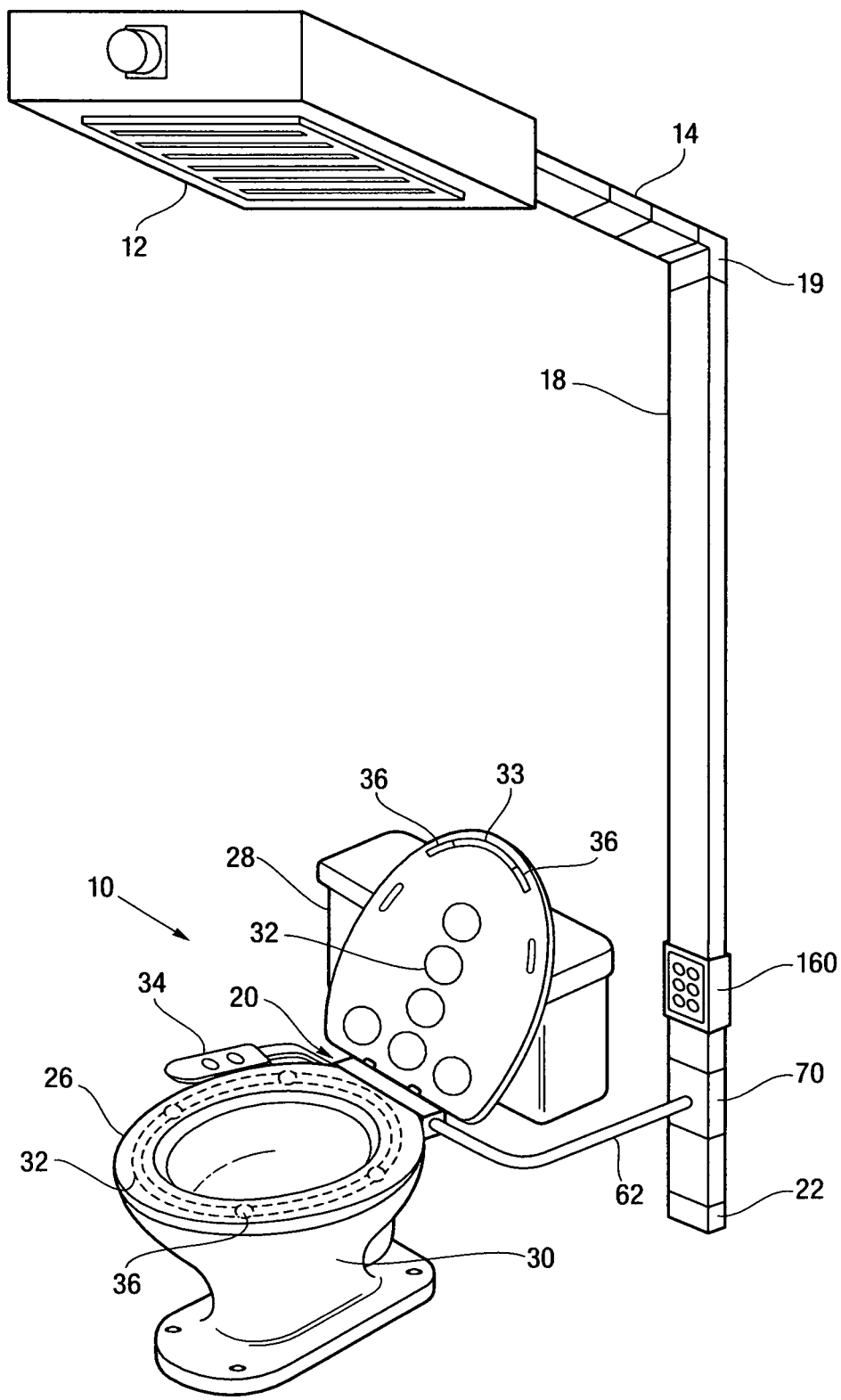
FIG. 1 shows a perspective view of an embodiment of the smart toilet system of the present disclosure.

The presently disclosed invention is described with specificity to meet statutory requirements. But, the description itself is not intended to limit the scope of this patent. Rather, the claimed invention might also be presented in other aspects, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described. The word "approximately" as used herein means within 5% of a stated value, and for ranges as given, applies to both the start and end of the range of values given.

In the following description, numerous specific details are set forth to provide a thorough understanding of the invention. But, the present invention may be practiced without these specific details. Structures and techniques that would be known to one of ordinary skill in the art have not been shown in detail, in order not to obscure the invention. Referring to the figures, it is possible to see the various major elements constituting the apparatus of the present invention.

The present subject matter discloses aspects of a smart toilet system 10. At a high level of overview, the smart toilet system 10 of the present invention comprises components designed to be fit in, on, above, or under a toilet seat, or to replace a toilet seat, bidet components, health monitoring components, ventilation or hygiene components, and communications and/or control components.

With reference to the drawings, various embodiments of a smart toilet system 10 will now be described.

In one aspect, when the sensors indicate a user is seated several processes are performed automatically or on (voice or remote) demand. The user and the seat are warmed by the Light Emitting Diodes (LED). The embedded varied sensors disclose the user's temperature, weight, BMI, HBP, and other heartbeat readings. The toilet seat digitally analyzes and documents the user's waste. The seat provides the user's bottom and back with infrared light therapy from the seat and cover. The center top of the closed seat cover provides the user with hair removal technology for better hygiene, while refurbishing the skin on the bottom private area. The lower bidet part of the seat provides a front and rear warm water adjustable sprayer with attachable vessels, which may be insulated and/or may be used for heating of fluids (i.e. water) supply. The seat provides a hygienic hands-free wiping mechanism with an automatic tissue feeder for the disabled and Obese users. The smart toilet system provides the users with an automatic flushing system. All data may be transferred to a mobile app, implemented in the remote control 84, and/or to an optional Smart Mirror which may be complementary to the present disclosure.

Definitions: As used herein, the term "ORG" means Odor Removal Gasket, and the gasket houses the secondary control center of the smart toilet system, which may comprise, enclose, surround, encapsulate, contain, or encompass some or all of the components of the smart toilet system 10, such as, but not limited to, mechanical components, plumbing components, and electrical components, including sensors such as, but not limited to, BMI sensors, weight sensors, motion sensors, infrared or near infrared lights, and one or more lighting elements, adapted to support lights of the same or different colors, and may include thermo-optical imaging sensors or components, and may have a receiver on a toilet seat or a toilet lid. Any of the foregoing sensors and components, and any of the sensors or components disclosed herein, may be low profile and/or printed onto a toilet seat or toilet lid, and where printed, may be printed with a graphite-based printer film.

Figure 28:
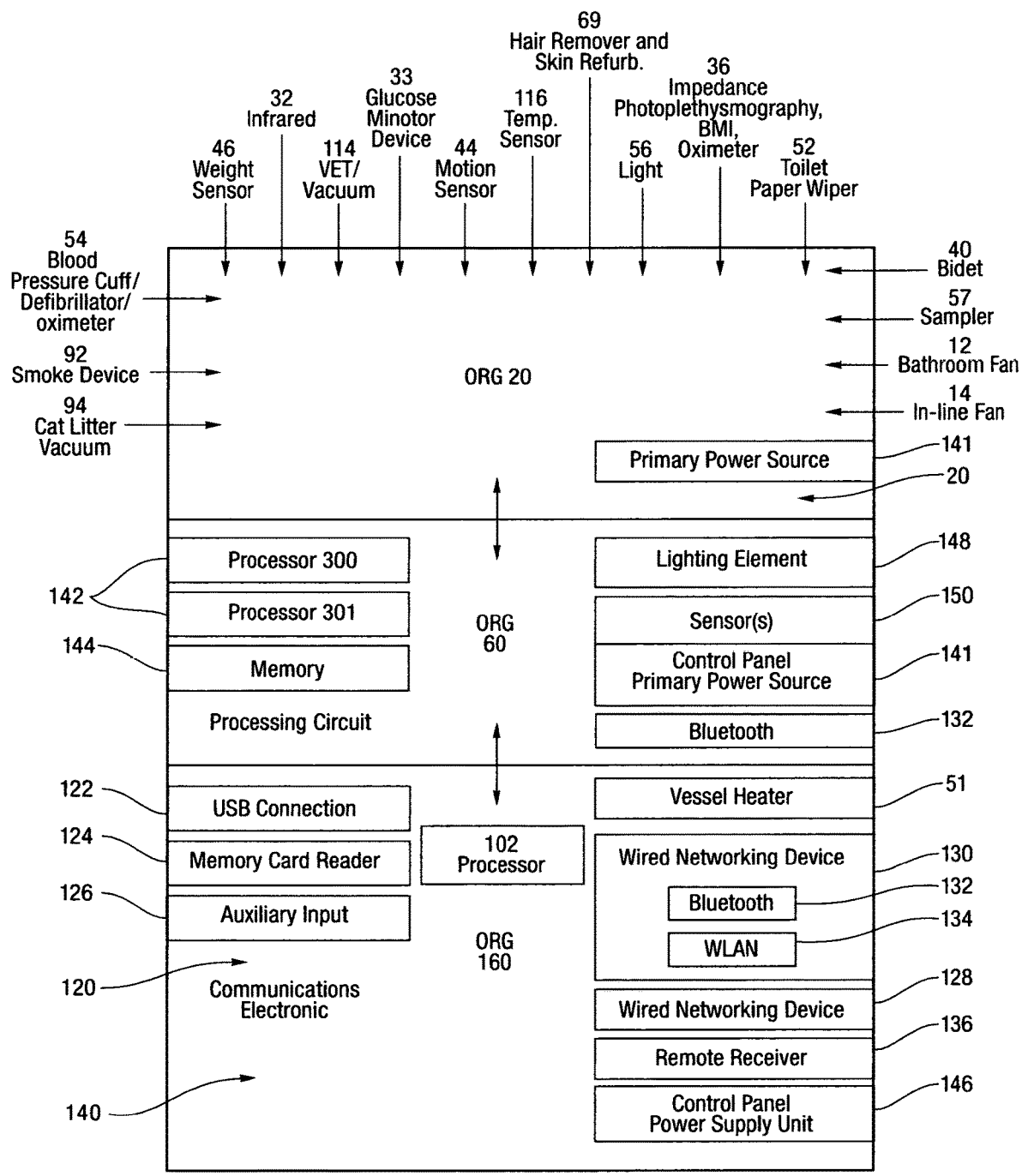
FIG. 28 shows a block diagram of the electrical components of selected portions of the smart toilet system of the present disclosure.

Some of the electrical components that may be housed within the ORG 20 are illustrated in the block diagram best seen in FIG. 28. As used herein, bullseye arrangement intense pulse light 69 means the grouping of an intense Pulse light hair remover with the infrared coagulation for skin refurbishing. A bullseye arrangement intense pulse light 69 may be located at the center, top of the closed toilet seat cover. The user can squat their private areas on top of the bullseye for hygiene and removal of hairs that harbor bacteria and waste.

FIG. 1 is a perspective view of an embodiment of the smart toilet system 10 described herein, the drawing showing a toilet bowl 30, a toilet seat 26, a plurality of infrared lights 32, a sticker attachment 35 connected by printed electronics, lights, electrode designs with AI performs Transdermal Optical Imaging (TOI) to reflect light deep off the skin for digital biomarkers, wherein the sticker attachment 35 may be related to a smooth flush finish 31, and wherein the sticker attachment 35 may comprise the plurality of infrared lights 32, the glucose monitor 33, and a plurality of impedance photoplethysmography sensors 36, and may comprise the smooth flush finish 31. The smart toilet system 10 may further comprise an ORG 20 with a user arm controller 34, a vacuum exhaust tubing (VET) 18 a VET arm connector 62, a control box 160, a plurality of in-apparatus fans 14, and a bathroom exhaust fan 12.

Figure 2A:
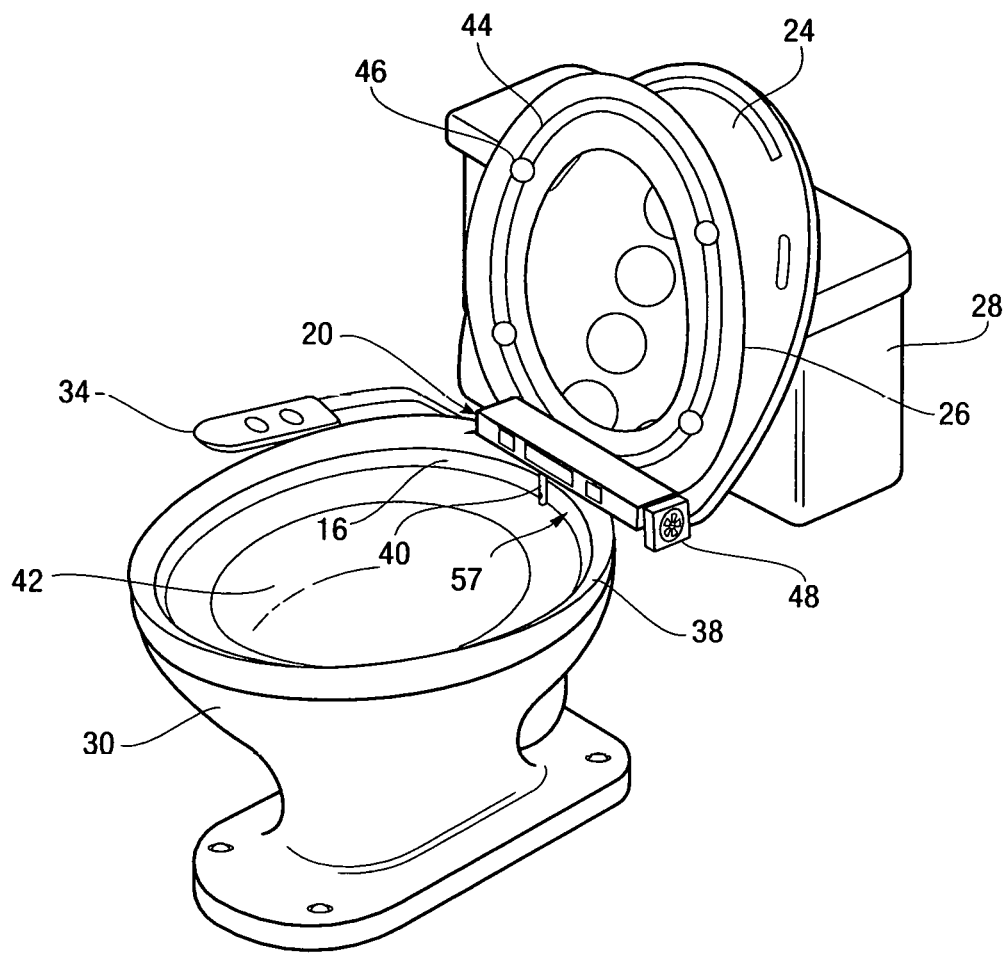
FIG. 2A shows a perspective view of an embodiment of the smart toilet system of the present disclosure.

FIG. 2A shows a perspective view of the smart toilet system of FIG. 1. FIG. 2A shows the smart toilet system 10 with the toilet seat 26 up and showing the bottom side of the ORG 20 with a user arm controller 34 and a fan deodorizer 48 where it would lie in context of the standard toilet.

Figure 2B:
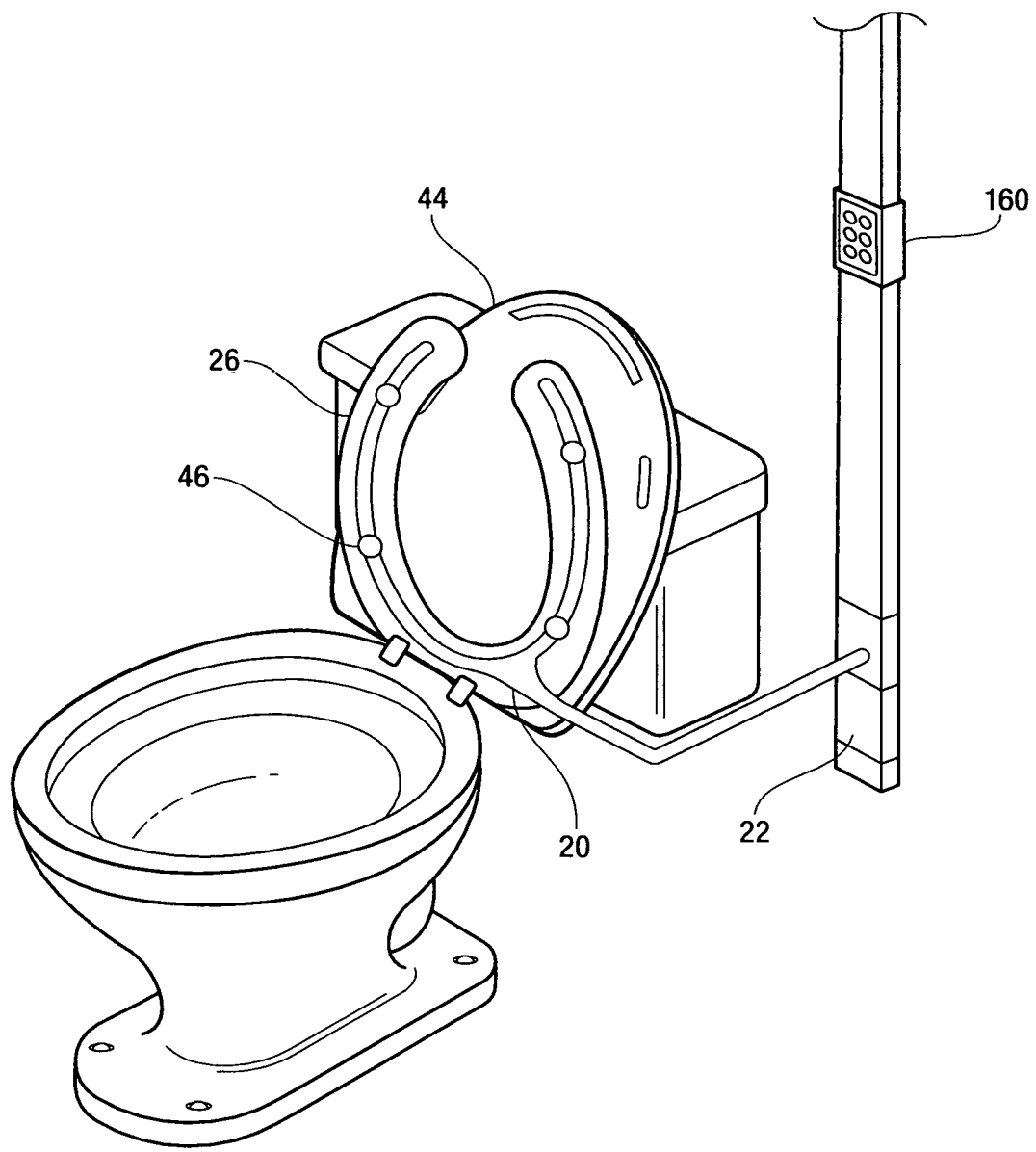
FIG. 2B shows a perspective view of an embodiment of the smart toilet system of the present disclosure, with selected components shown in an exploded view.

FIG. 2B shows the optional U-shaped, one piece vacuum exhaust tubing ORG 20 of FIG. 1, showing the toilet seat up 26 and showing the open front portion of the ORG supported by the toilet seat. The front open-end tips are illustrated to contain the motion sensors 44 for the lighting elements 56.

Figure 3:
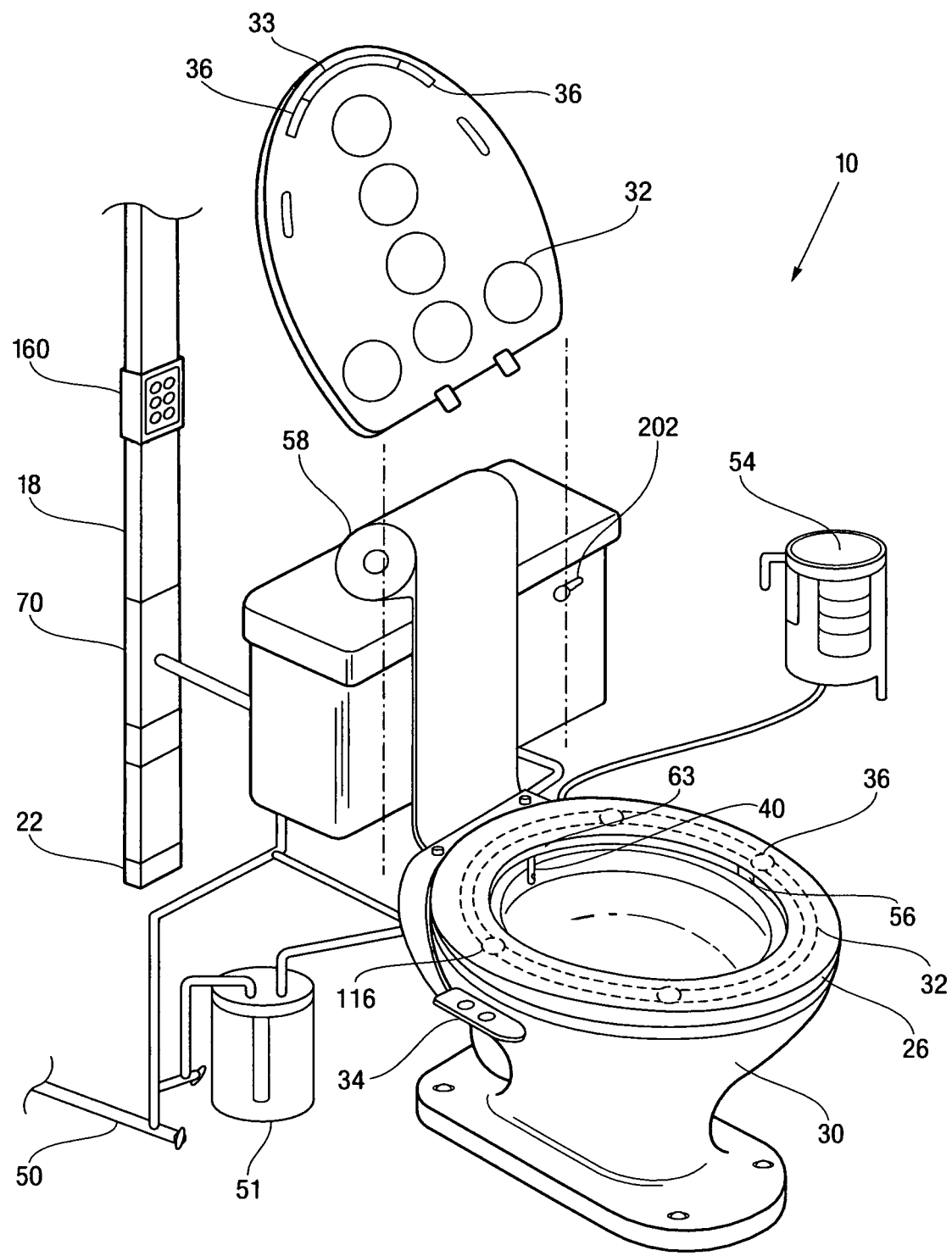
FIG. 3 shows a different perspective view of an embodiment of the smart toilet system of the present disclosure.

FIG. 3 shows the smart toilet system 10 of FIG. 1, wherein toilet seat is laying parallel to the toilet bowl. Plumbing system is depicted along with the user arm controller 34 and vacuum exhaust tubing VET 18. Optional attachments for the smart toilet system 10 include, but are not limited to, a toilet paper wiper system 52, an auto-flush handle 2, and a vessel 51, and an electronic blood pressure cuff defibrillator-electrode 54, which electronic blood pressure cuff-defibrillator electrode 54 may comprise a blood pressure cuff and/or an oxygenator and/or a defibrillator.

Figure 4:
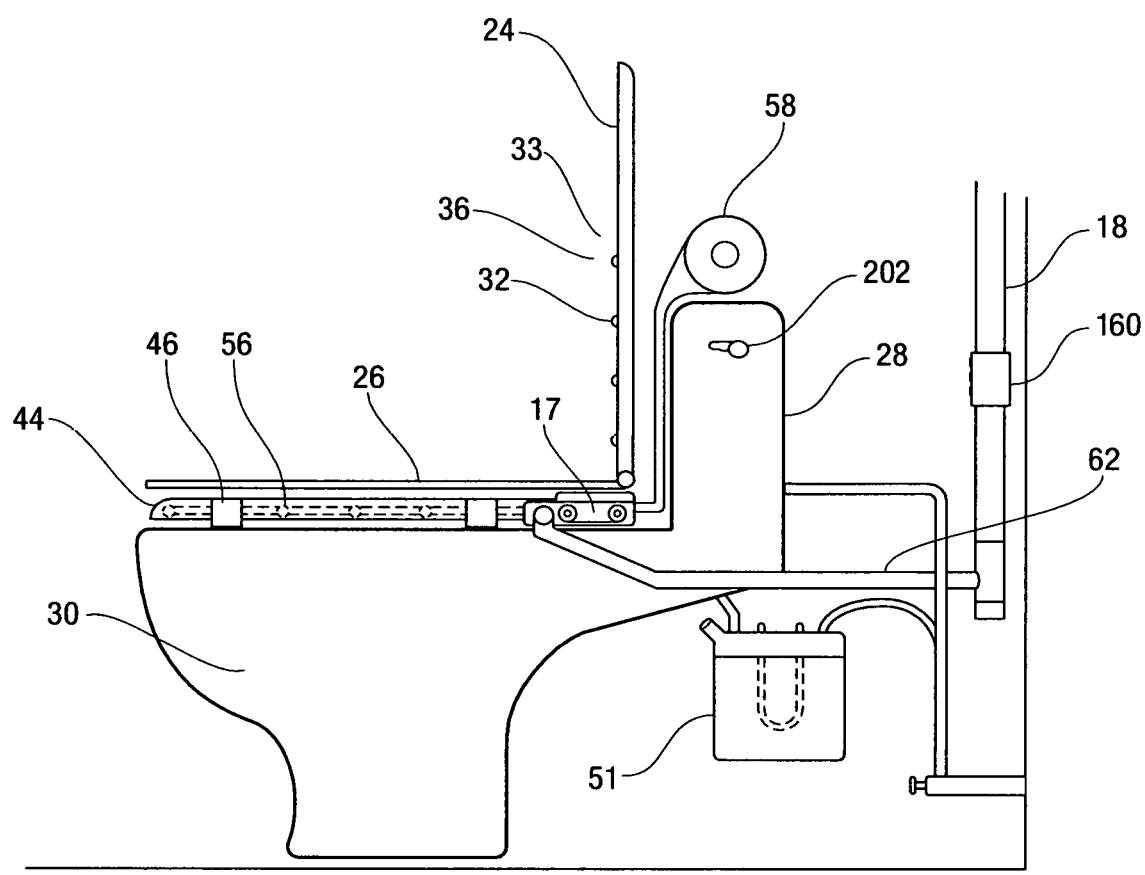
FIG. 4 shows a side elevation view of an embodiment of the smart toilet system of the present disclosure.

FIG. 4 shows the smart toilet system 10 of FIG. 1, wherein a side elevation view shows the toilet bowl 30, the toilet seat 26, ORG 20, infrared lights 32, toilet seat cover 24, vessel 51 for the bidet, and a toilet user's wiper system 52.

Figure 5:
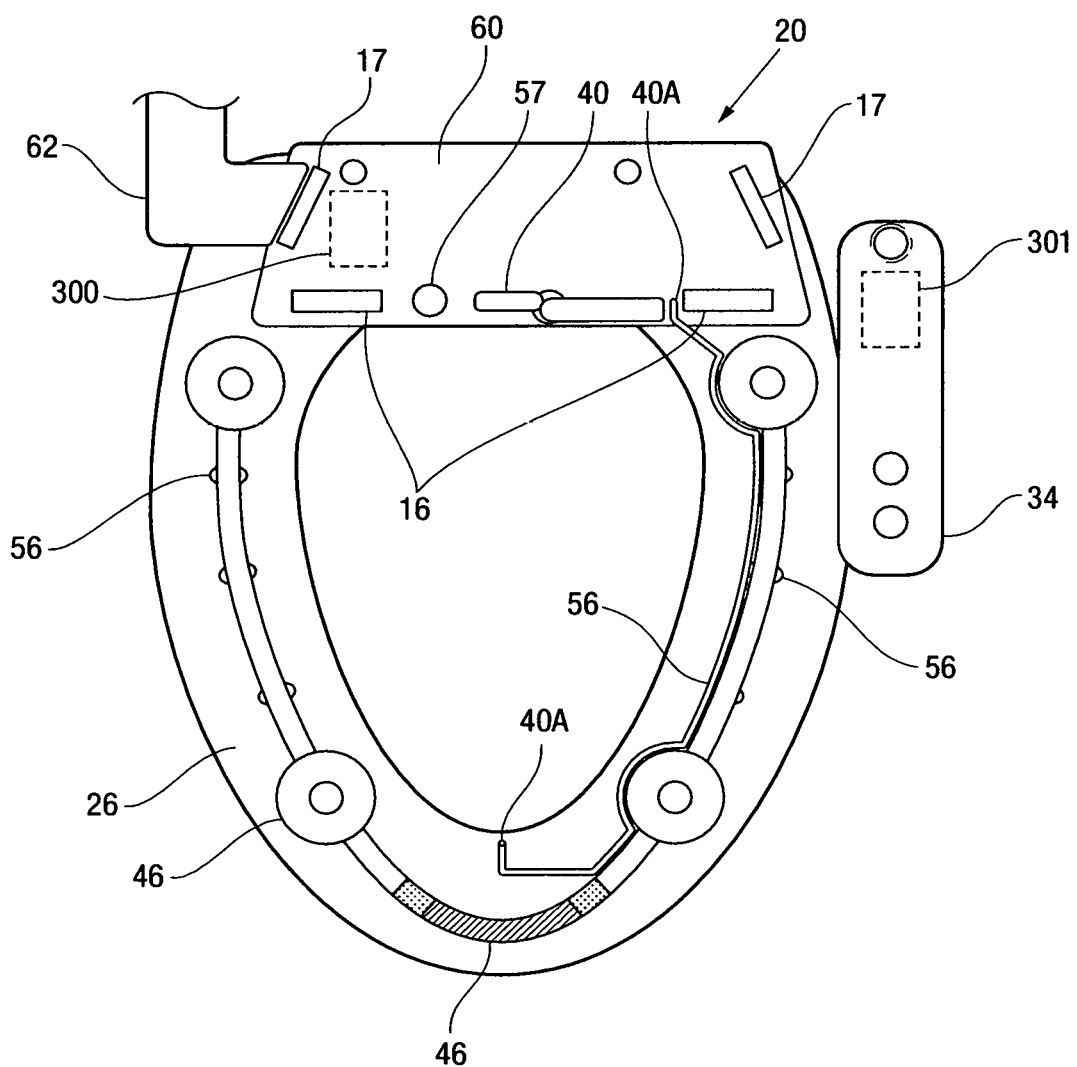
FIG. 5 shows a bottom plan view of selected portions of the smart toilet system of the present disclosure.

FIG. 5 shows the bottom view of the front and rear portions of the ORG 20 with the user arm controller connected to the vacuum exhaust tubing of the smart toilet of FIG. 1. FIG. 5 shows the bottom view of ORG 20 as it is attached on the bottom of the toilet seat with its bottom facing upwards. The front and rear portions of the ORG 20 are depicted to include the lighting elements 56, motion sensors 44, optical sensor waste analyzer 57 which may scan and/or analyze, digitally or otherwise, one or more samples of a user's urine or fecal matter, a user arm controller 34, a rear bidet sprayer head 40 and a front bidet sprayer head 40a, and body weight sensors 46. The VET arm 62 is shown where it would lie in context relative to the ORG 20 housing 60. FIG. 5 also depicts an ORG-processing-unit 300 for the ORG 20 within the housing 60 of the ORG 20 in dotted lines; the ORG processing-unit 300 may be comprised within a processor 142. FIG. 5 shows UAC-processing-unit 301 of the user arm controller 34 in dotted lines within the user arm controller 34; the UAC-processing-unit 301 may be comprised within the processor 142.

Figure 6:
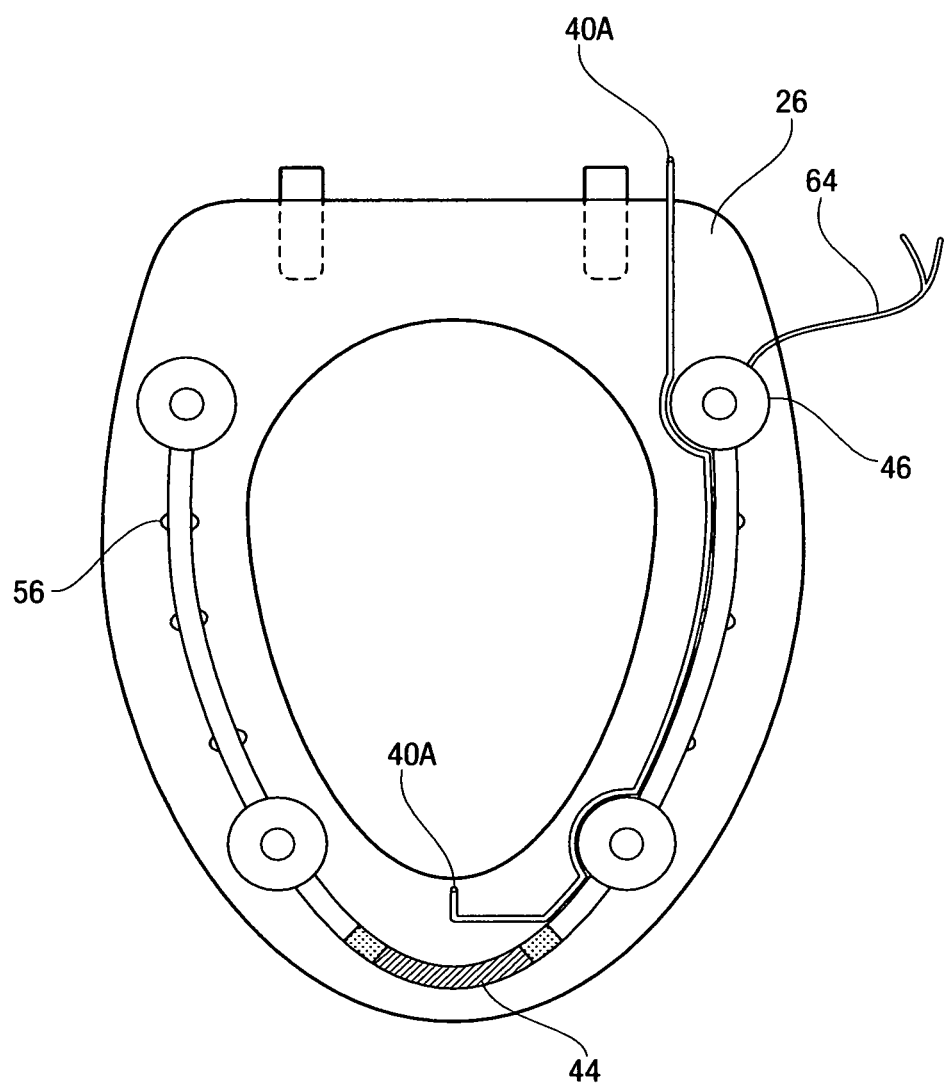
FIG. 6 shows a bottom plan view of selected portions of the smart toilet system of the present disclosure.

FIG. 6 shows the bottom view of the front portion of the ORG of the smart toilet of FIG. 1. FIG. 6 shows the lighting elements 56, the motion sensors 44, a plurality of body weight sensors 46, the front bidet sprayer head 40a, dedicated to the wiper, and wires attached to the bottom of the toilet seat.

Figure 7:
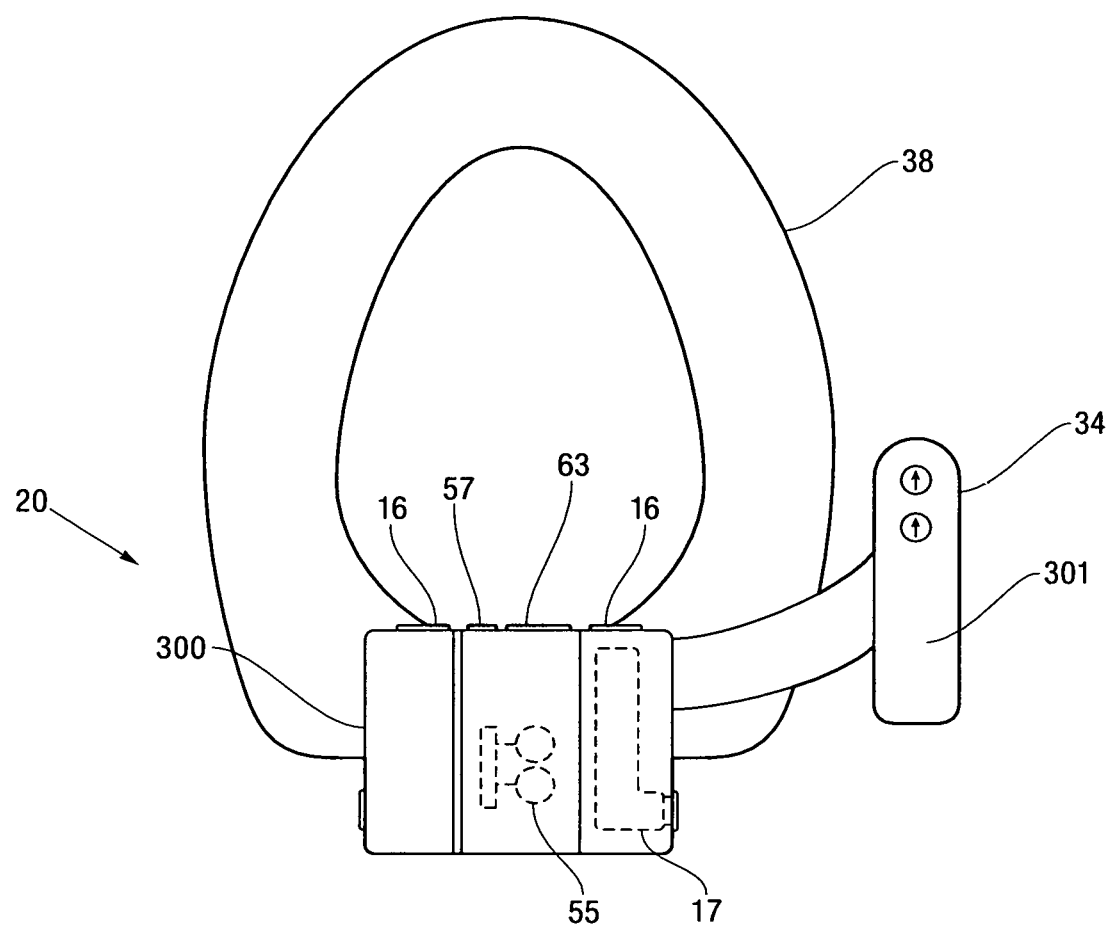
FIG. 7 shows a top plan view of selected portions of the smart toilet system of the present disclosure.

FIG. 7 shows the top-down view of the rear of the ORG 20 housing 60 portion of the ORG 20 of the smart toilet of FIG. 1. The rear portion of the ORG is depicted along with the toilet bowl lip 38, the optical sensor waste analyzer 57, the user arm controller 34, and the rear bidet sprayer head 40. The rear odor openings 17 where the VET arm (not illustrated) or fan deodorizer (not illustrated) could be attached or plugged is depicted on either side of the ORG 20. In some aspects of the present disclosure, the optical sensor waste analyzer 57 may be used to detect and/or analyze materials related to diagnosis or treatment of medical conditions or diseases, including but not limited to COVID-19 and comorbidities for COVID-19, and including but not limited to viral particles, bacterial cells or fragments thereof, or biomarkers or proxies for the foregoing.

Figure 8:
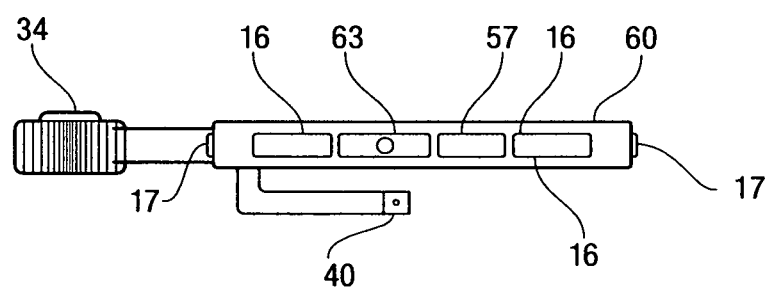
FIG. 8 shows a front perspective view of a portion of the smart toilet system of the present disclosure.

FIG. 8 shows the top view of the rear portion of the ORG of FIG. 7, wherein the side elevation shows the user control arm, ORG housing, and bidet.

Figure 9:
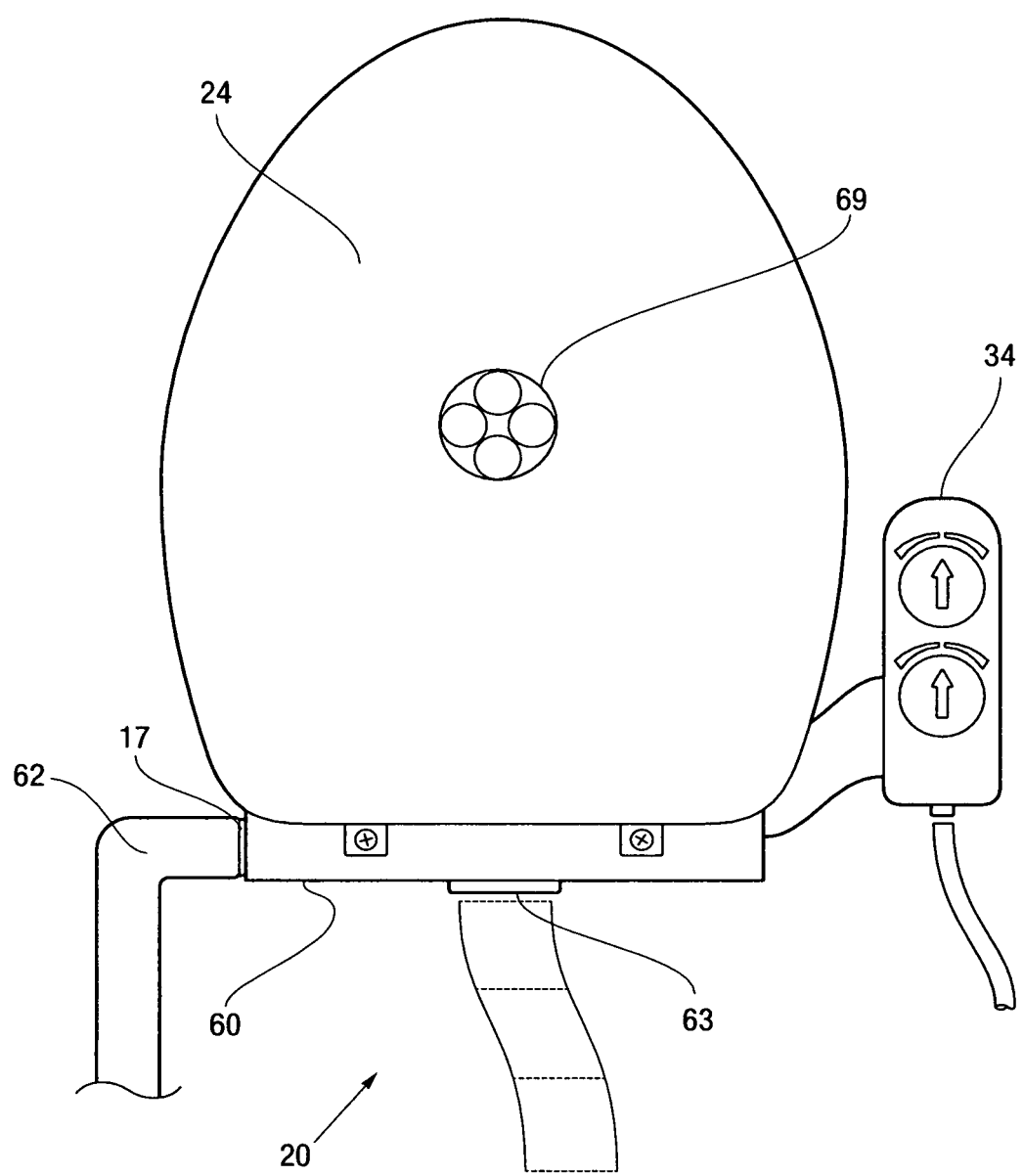
FIG. 9 shows an exploded top perspective view of selected portions of the smart toilet system of the present disclosure.

FIG. 9 shows the rear portion of the ORG of FIG. 7, wherein the top-down elevation shows the user control arm in its relationship to the toilet seat cover with a bullseye arrangement intense pulse light 69 with infrared coagulation for perineum hair removal and/or skin refurbishing, and VET arm 62.

Figure 10A:
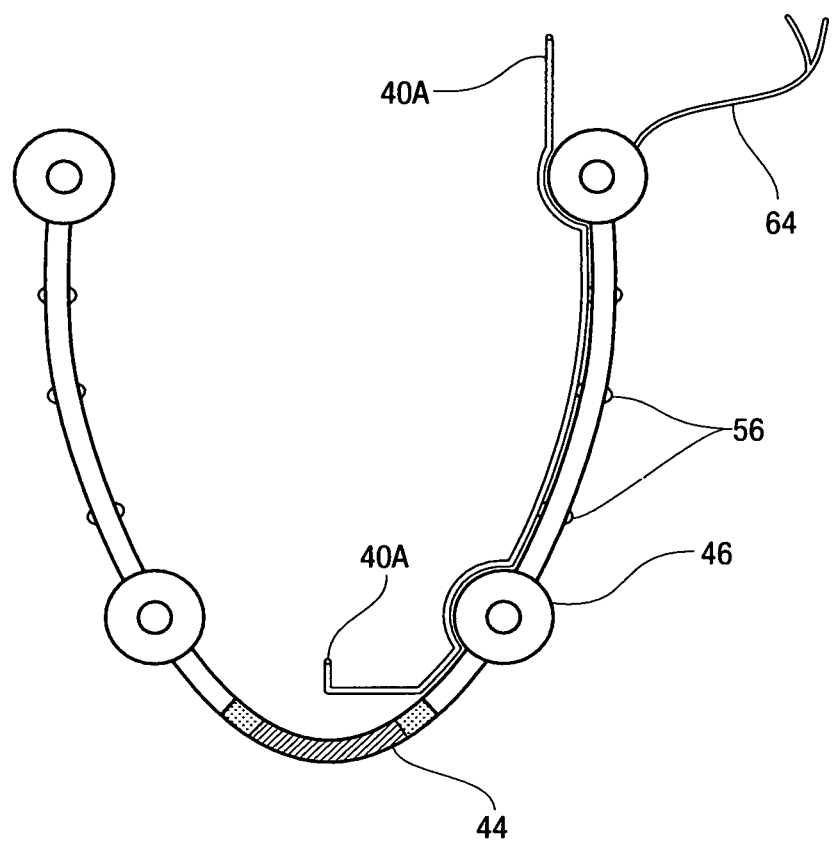
FIG. 10A shows a top plan view of selected portions of the smart toilet system of the present disclosure.

FIG. 10A shows the front portion of the ORG 20 of FIG. 6. FIG. 6 shows the wiring of the front portion of the ORG 20. The front portion of the ORG 20 is wired to include the lighting elements, motion sensor, and body weight sensors and the front bidet sprayer head 40a.

Figure 10B:
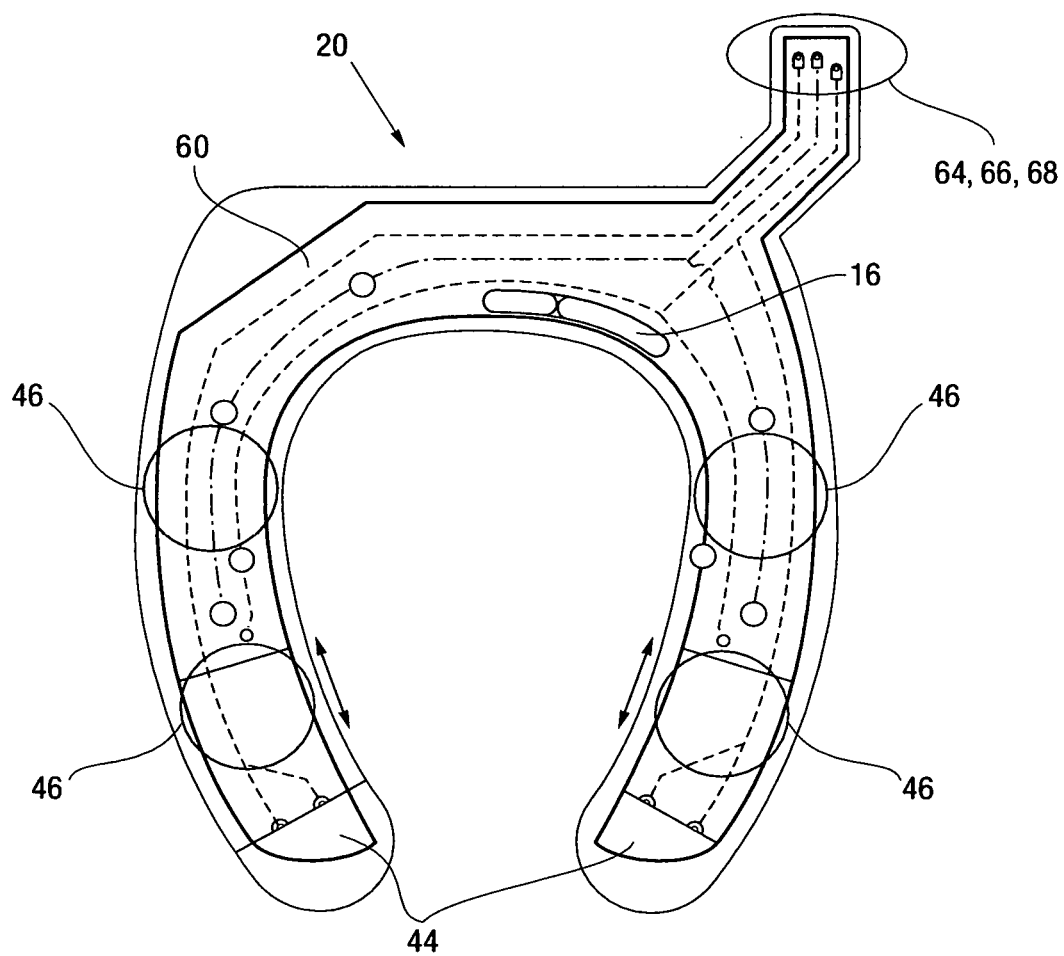
FIG. 10B shows a top plan view of selected portions of the smart toilet system of the present disclosure.

FIG. 10B shows the front portion of the ORG 20 of FIG. 2B, wherein the front portion of the ORG 20 contains a possible housing shell. FIG. 10B shows the wiring of the front portion of the ORG 20. The front portion of the ORG 20 is wired to include the lighting elements, motion sensors, and body weight sensors.

Figure 11:
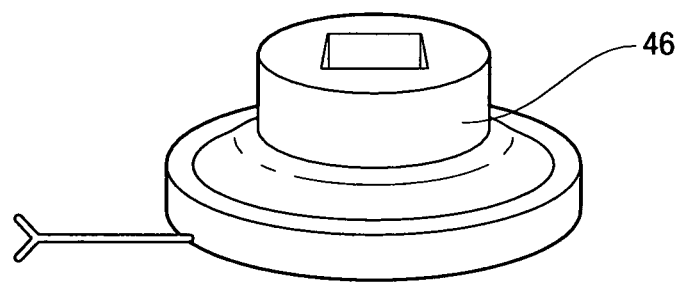
FIG. 11 shows an exploded perspective view of selected portions of the smart toilet system of the present disclosure.
Figure 12A:
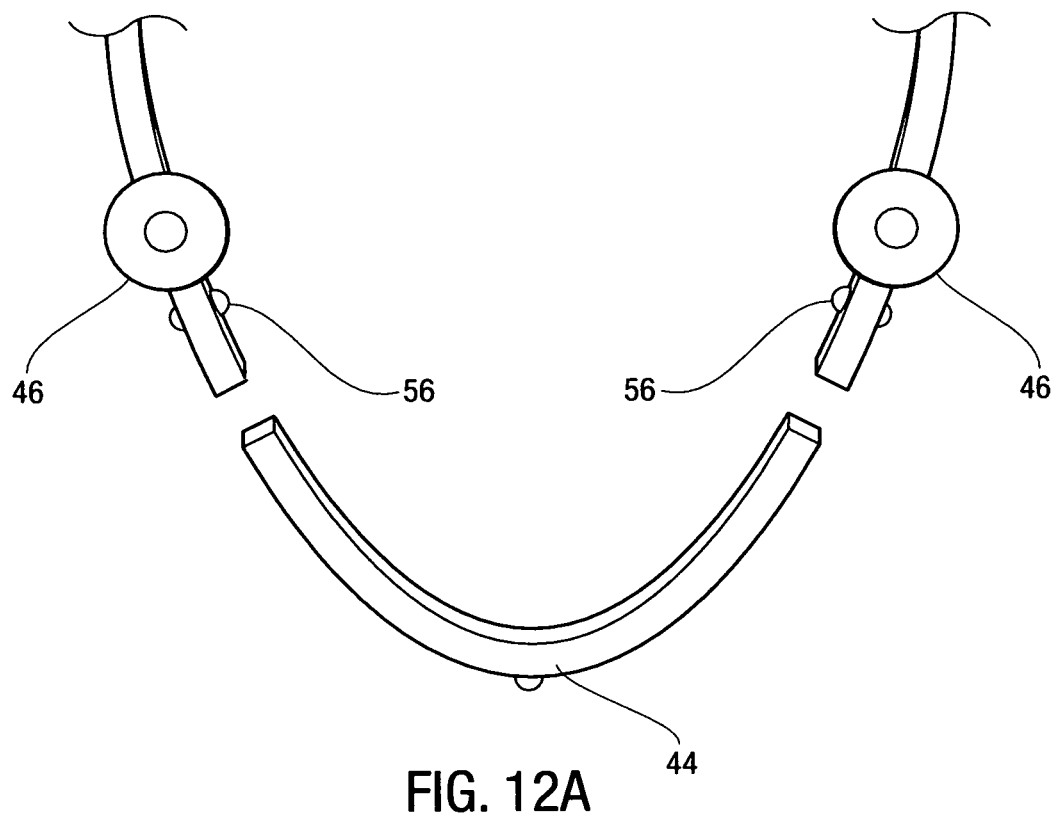
FIG. 12 shows an exploded perspective view of selected portions of the smart toilet system of the present disclosure.
Figure 12B:
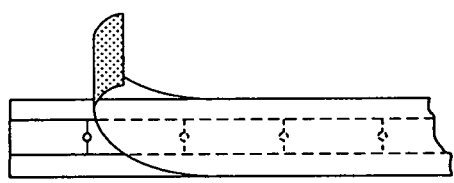
Figure 12C:
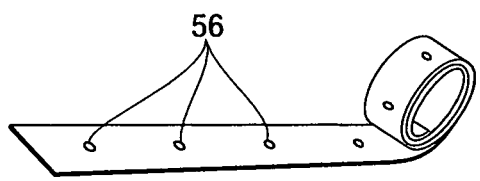
Figure 12D:

FIG. 11 shows the parts of the body weight sensors of the front portion of the ORG 20 of FIGS. 6 and 10B.

FIG. 12 shows the lighting elements as it sits on the front portion of the ORG of FIG. 2A, FIG. 2B, and FIG. 6, wherein the lights are depicted as strip lights.

Figure 13:
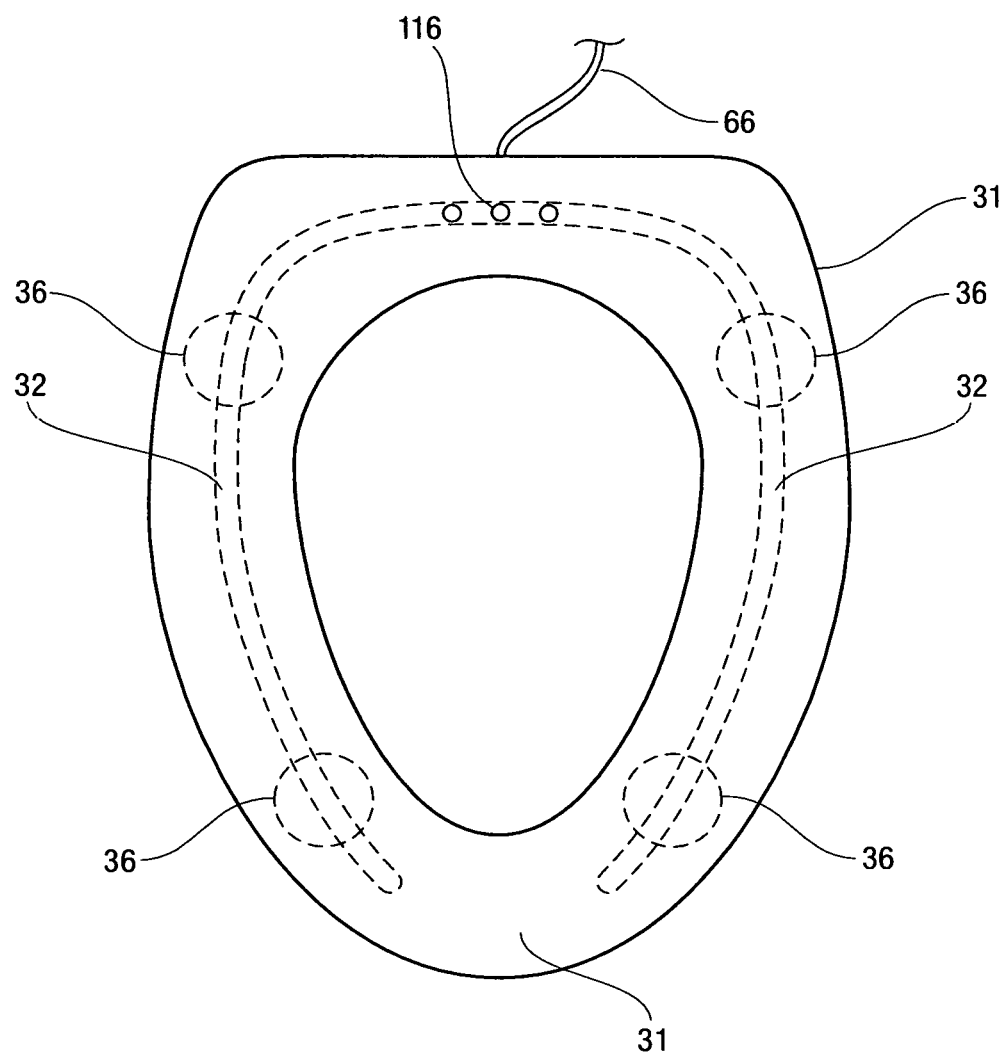
FIG. 13 shows a top plan view of selected portions of the smart toilet system of the present disclosure.

FIG. 13 shows the top-down view of the toilet seat with infrared lights 32, impedance photoplethysmography sensors 36, which are described below in greater detail, and temperature sensor of the smart toilet system of FIG. 1. FIG. 13 shows the possible wiring corresponding to the temperature sensors 116, impedance photoplethysmography sensors 36. The impedance photoplethysmography sensors 36 may be used to measure body mass index ("BMI").

Figure 14:
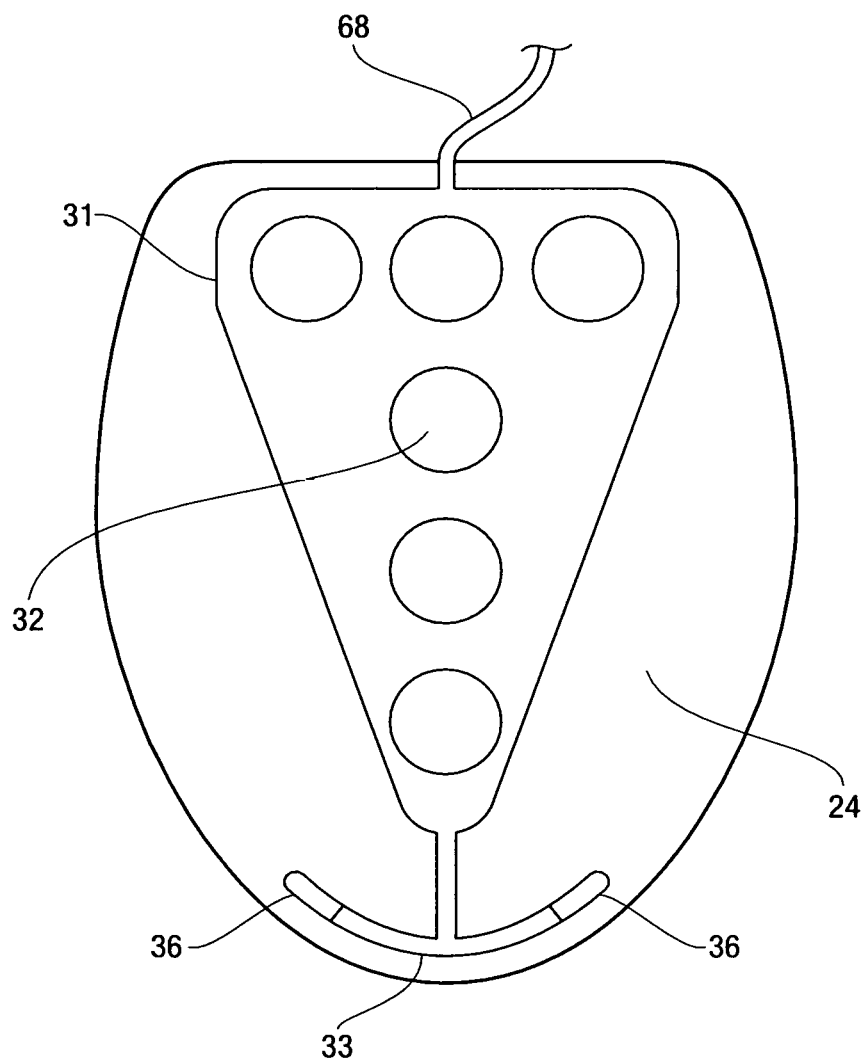
FIG. 14 shows a top plan view of selected portions of the smart toilet system of the present disclosure.

FIG. 14 shows the toilet seat cover of FIG. 3, wherein the bottom of the standard toilet seat cover is facing upwards. The infrared or near infrared stickers, electrodes, and glucose monitor depicted lining on top of the toilet seat cover as depicted. This carries the wiring for the bullseye-arrangement intense pulse light 69, which penetrates through cover to the other side, top side of cover.

Figure 15A:
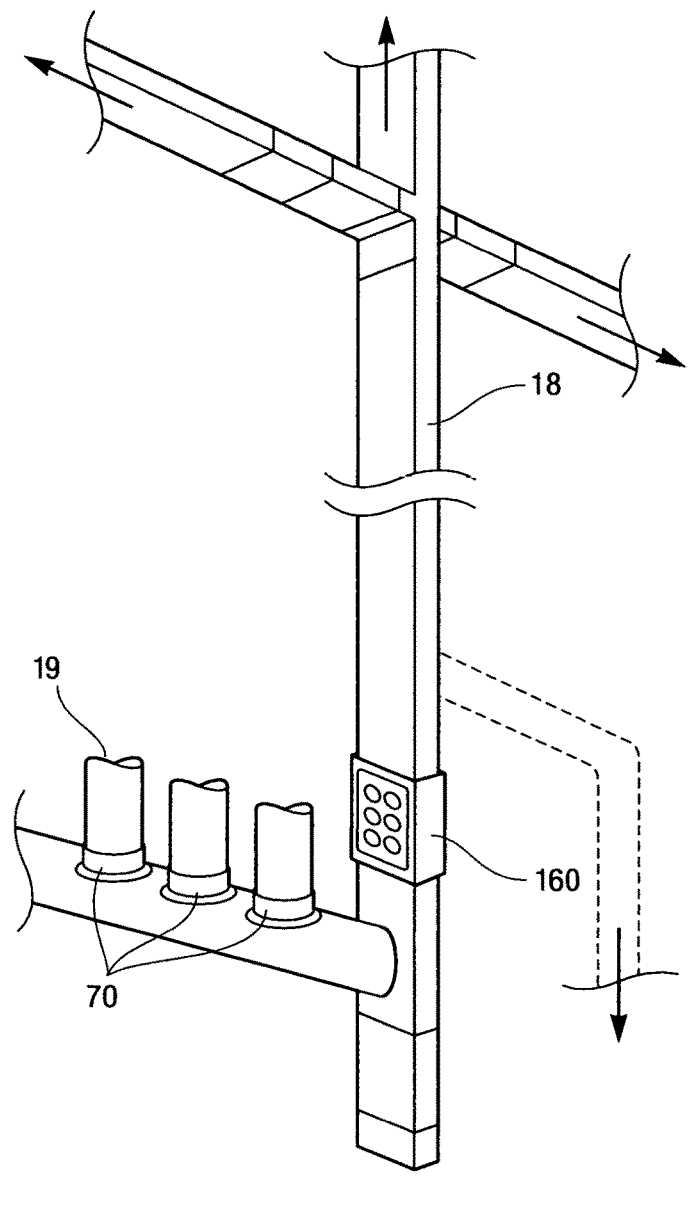
FIG. 15 shows side elevation views of selected portions of the smart toilet system of the present disclosure.
Figure 15B:
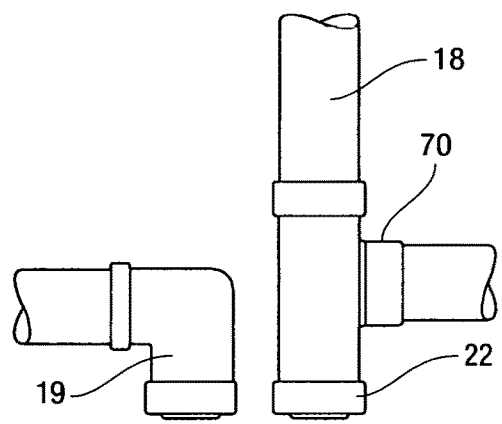

FIG. 15 shows the vacuum exhaust tubing, VET trap and fittings used in the vacuuming system of FIG. 1. Depicted are possible configurations of the vacuum exhaust tubing, VET trap 22, plumbing connection tee tubing 70, plumbing connection elbow tubing 19, and fittings of the vacuuming system 114.

Figure 16A:
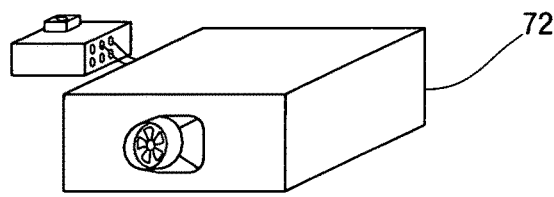
FIG. 16A shows multiple perspective views of selected portions of the smart toilet system of the present disclosure.

FIG. 16A shows varying perspective views of the bathroom ceiling fan boxes 72 of FIG. 1. The bathroom ceiling fan boxes 72 may comprise two fans: first, a main fan for humidity, and second, a dedicated or isolated fan for the VET 18 and primary power source 141. The bathroom ceiling fan boxes 72 may comprise a modified bathroom fan cover.

Figure 16B:
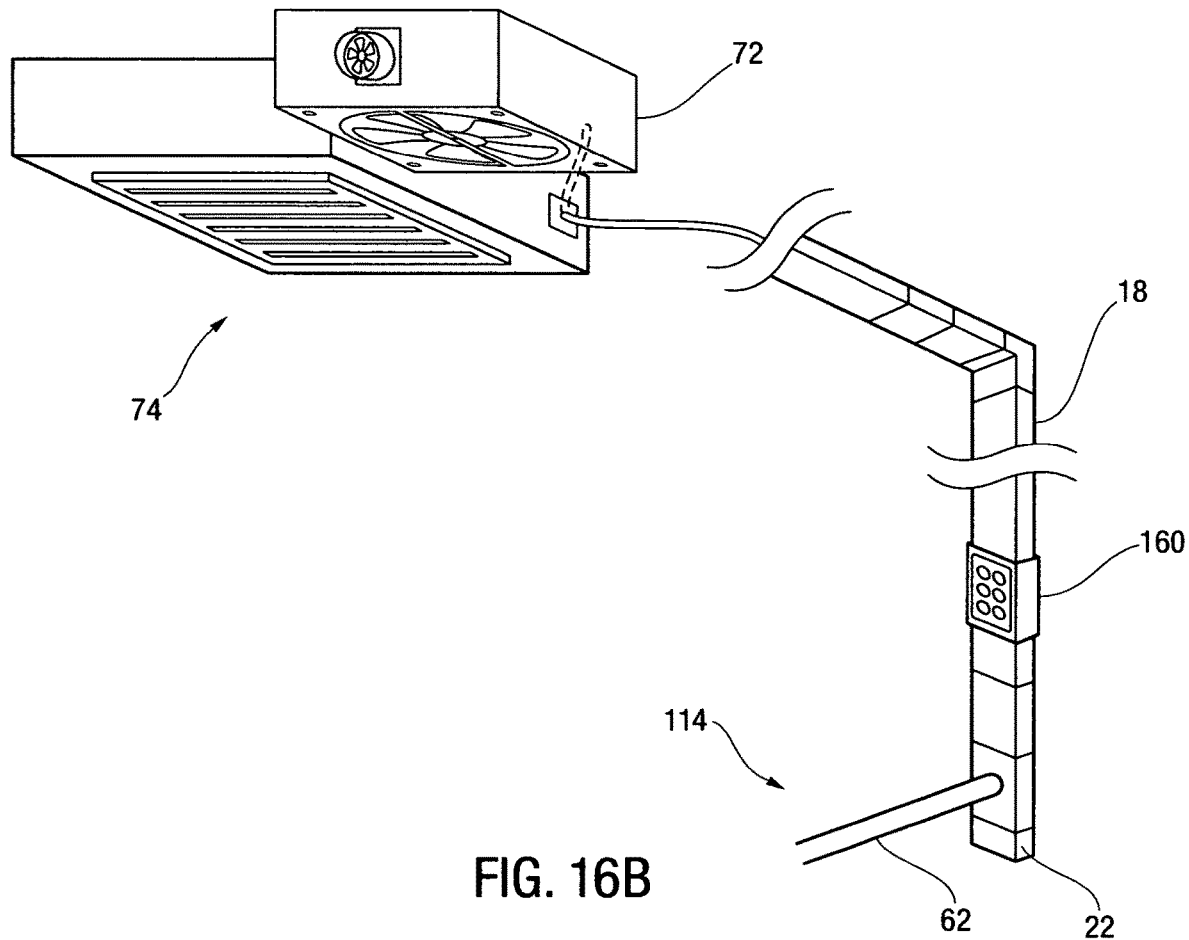
FIG. 16B shows a perspective view of selected portions of the smart toilet system of the present disclosure.

FIG. 16B shows the vacuuming system of FIG. 1, including the bathroom ceiling fan boxes 72, fan-blades 78, and bathroom fan cover 74 as they connect to the VET 18. The bathroom fan cover 74 has an option for a Bluetooth speaker modification. Power may be provided to the vacuuming system 114 from the bathroom ceiling fan boxes 72.

Figure 17:
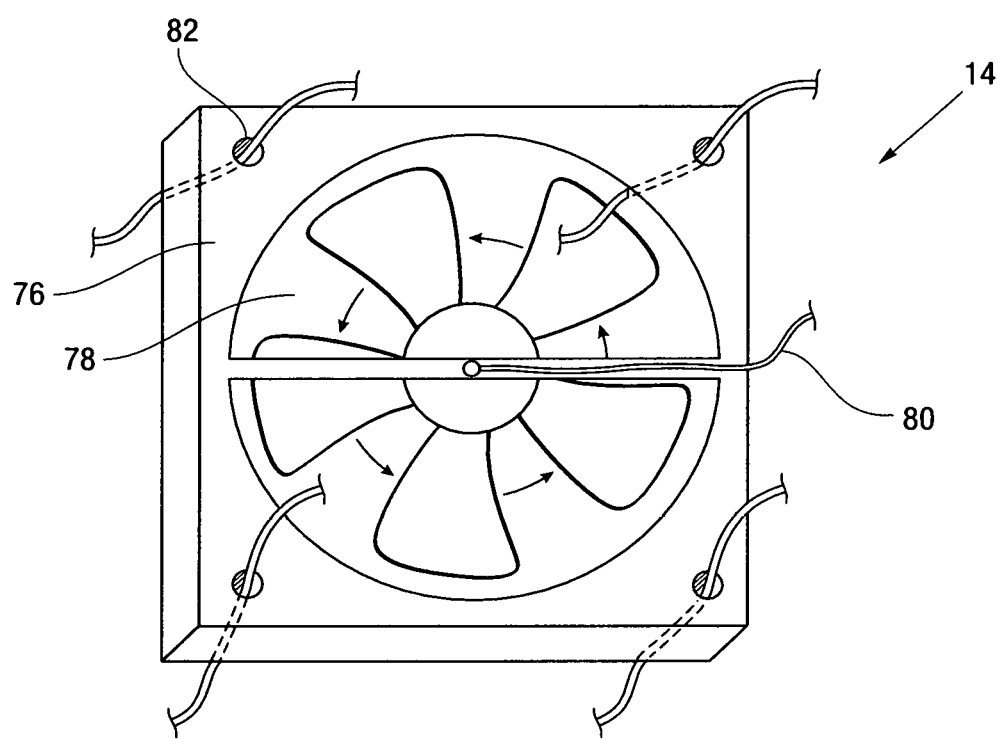
FIG. 17 shows a perspective view of selected portions of the smart toilet system of the present disclosure.

FIG. 17 shows front view of the in-apparatus fans 14 of FIG. 16B, wherein the in apparatus fans 14 is capable of connecting to the VET 18 or the vent of the bathroom ceiling fan boxes 72 as depicted in FIG. 16B.

Figure 18:
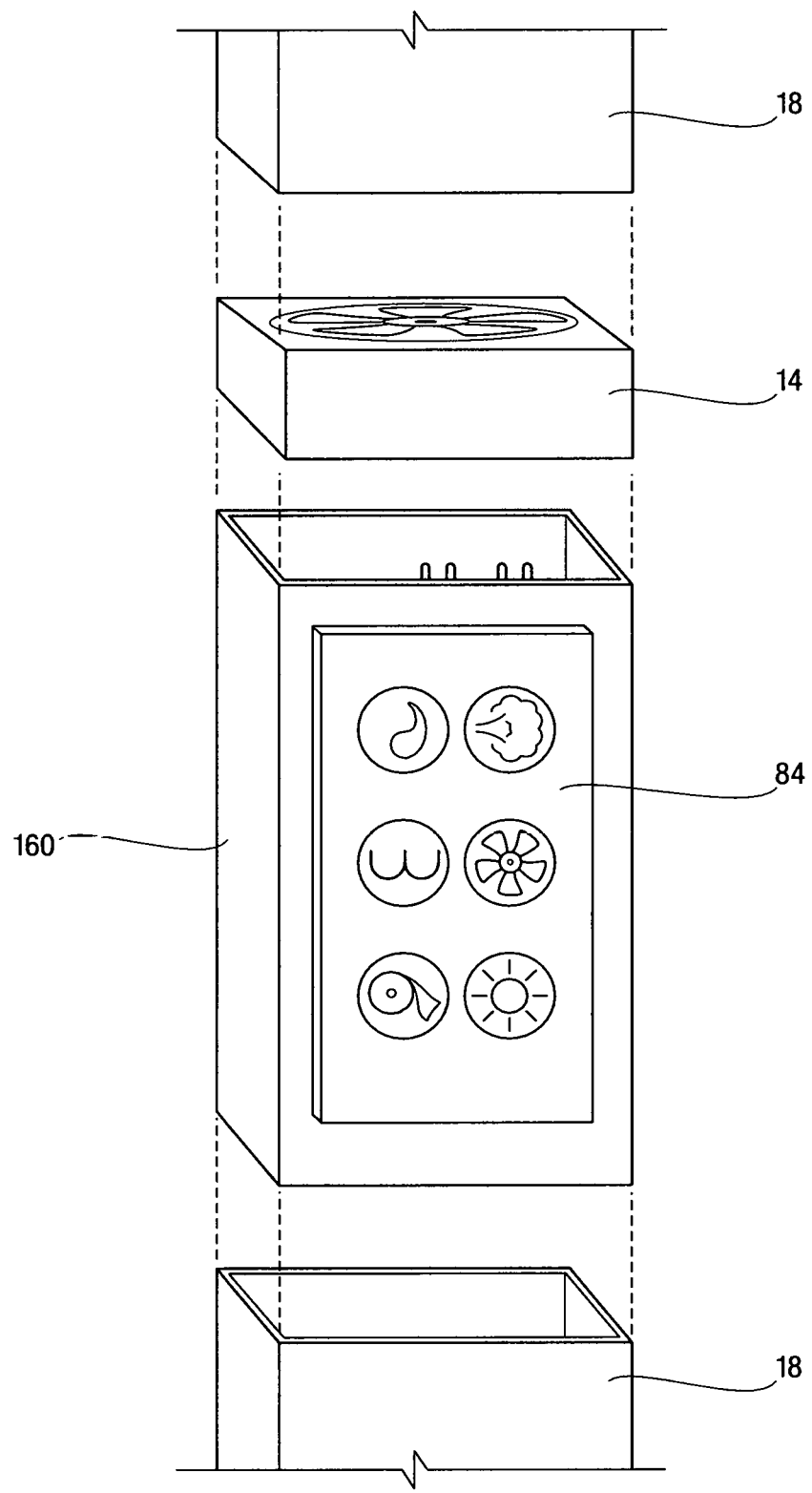
FIG. 18 shows a perspective view of selected portions of the smart toilet system of the present disclosure.

FIG. 18 shows a perspective view of the control box 160 of FIG. 1, wherein the control box 160 sits between portions of the VET 18. FIG. 18 shows the region of the control box 160 where the remote control can be docked for charging purposes. One of the plurality of in-apparatus fans 14 is depicted to fit within the control box 160 and one of the portions of the VET 18.

Figure 19:
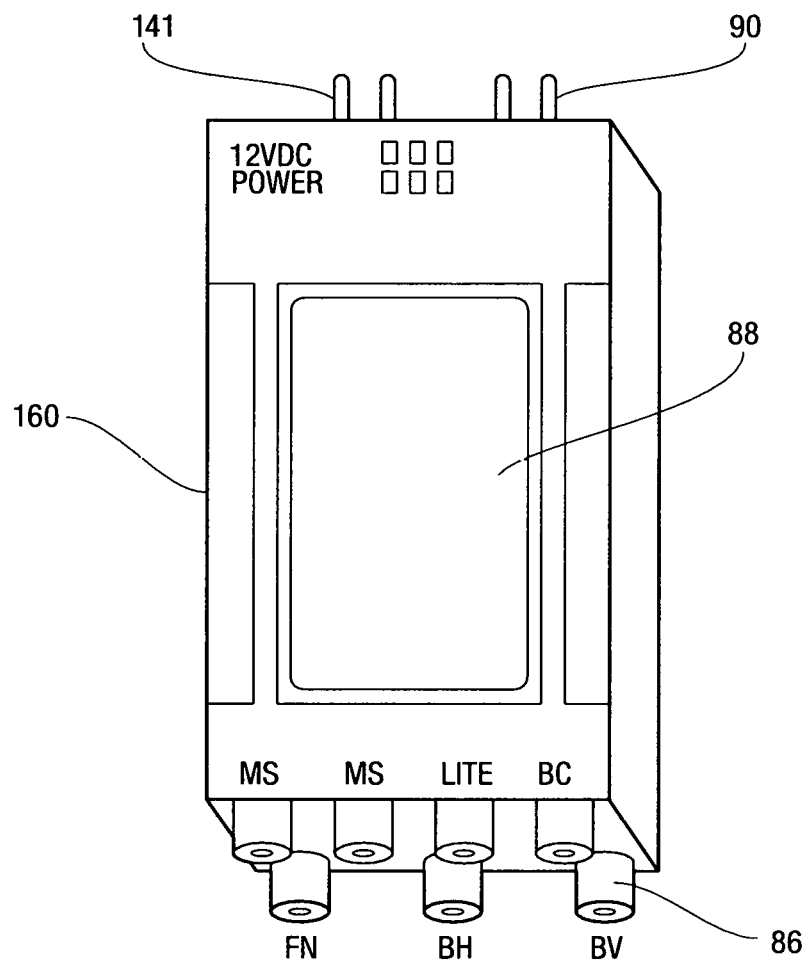
FIG. 19 shows a perspective view of selected portions of the smart toilet system of the present disclosure.

FIG. 19 shows the control box 160 of FIG. 18, wherein the control box 160 includes a region where the remote control 84 can sit to charge, DC/AC connections for the wires of the ORG 20, and wires for the power source of the control box 160.

Figure 20:
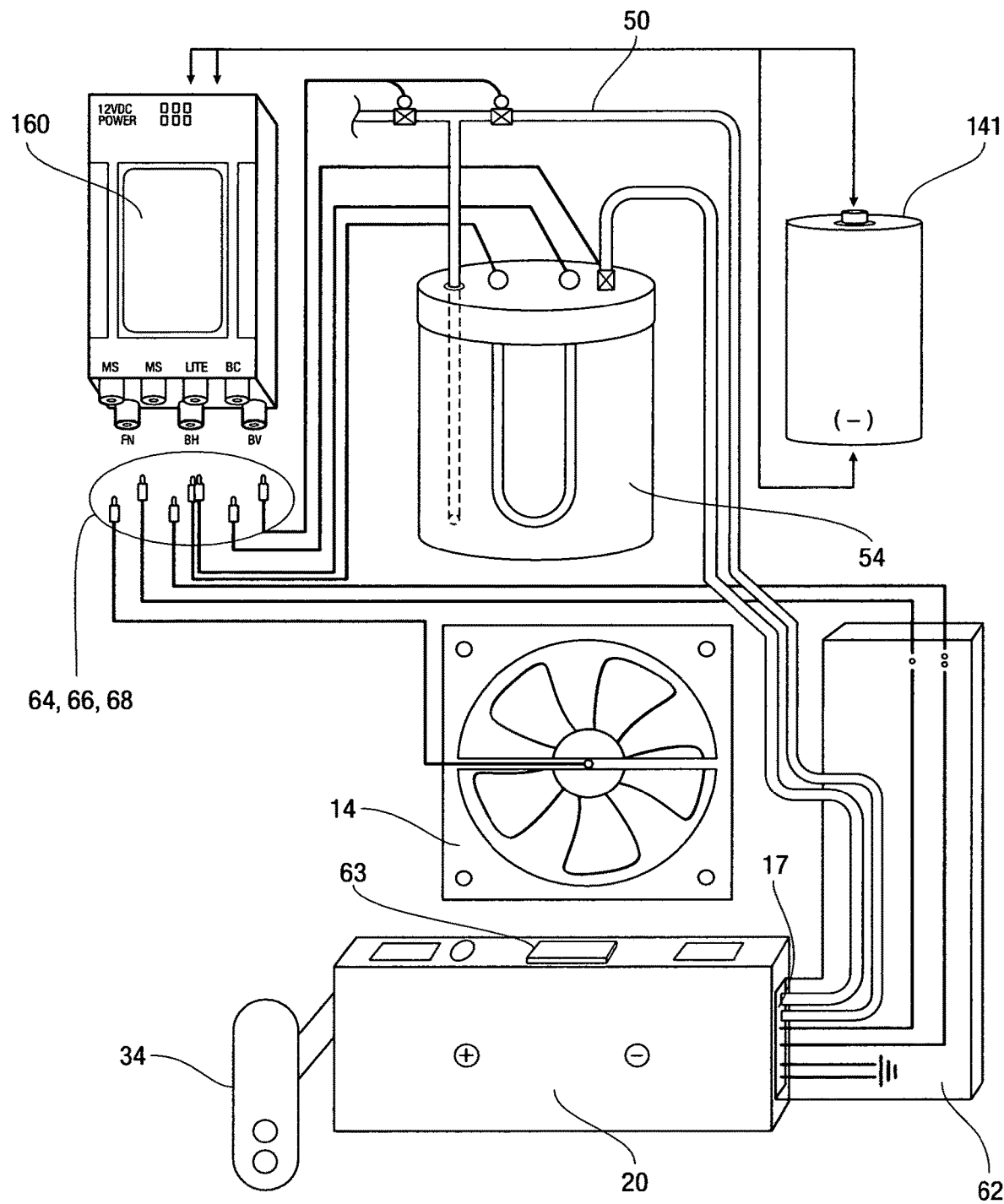
FIG. 20 shows an electrical wiring schematic of the smart toilet system of the present disclosure.

FIG. 20 shows the electrical wiring schematic of the smart toilet system 10 of FIG. 1, wherein the control box 160 communicates with the smart toilet system 10. The wiring of the rear end of the ORG 20 and the vessel 51 element of the bidet is depicted to connect to the control box 160.

Figure 21:
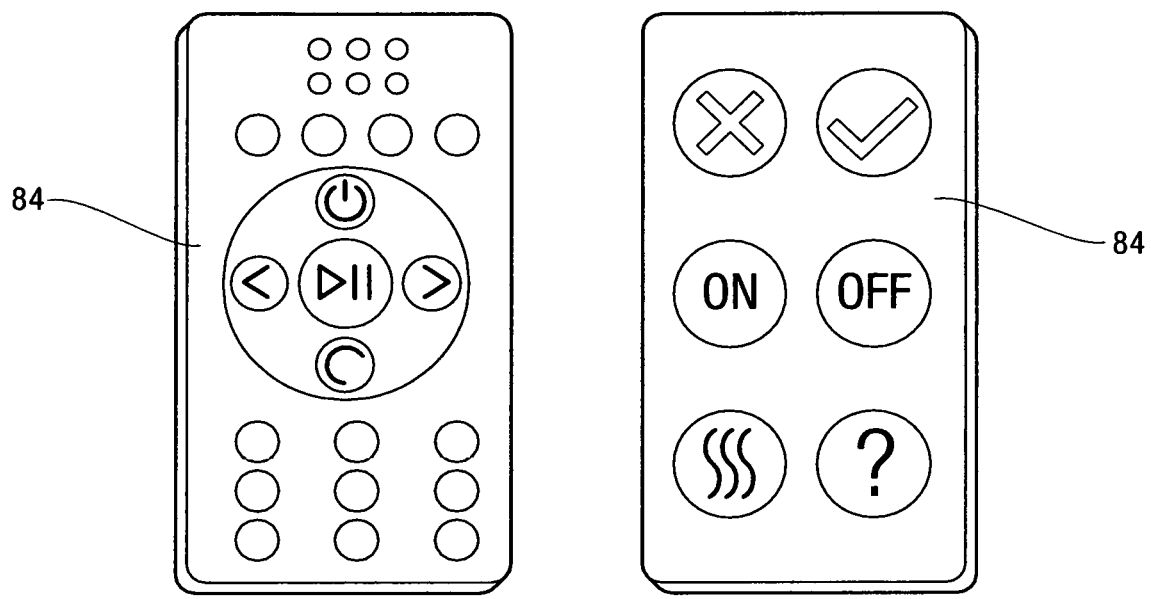
FIG. 21 shows two possible interfaces of the remote control of the smart toilet system of the present disclosure.

FIG. 21 shows the possible interfaces of the remote control 84 of FIG. 18.

Figure 22:
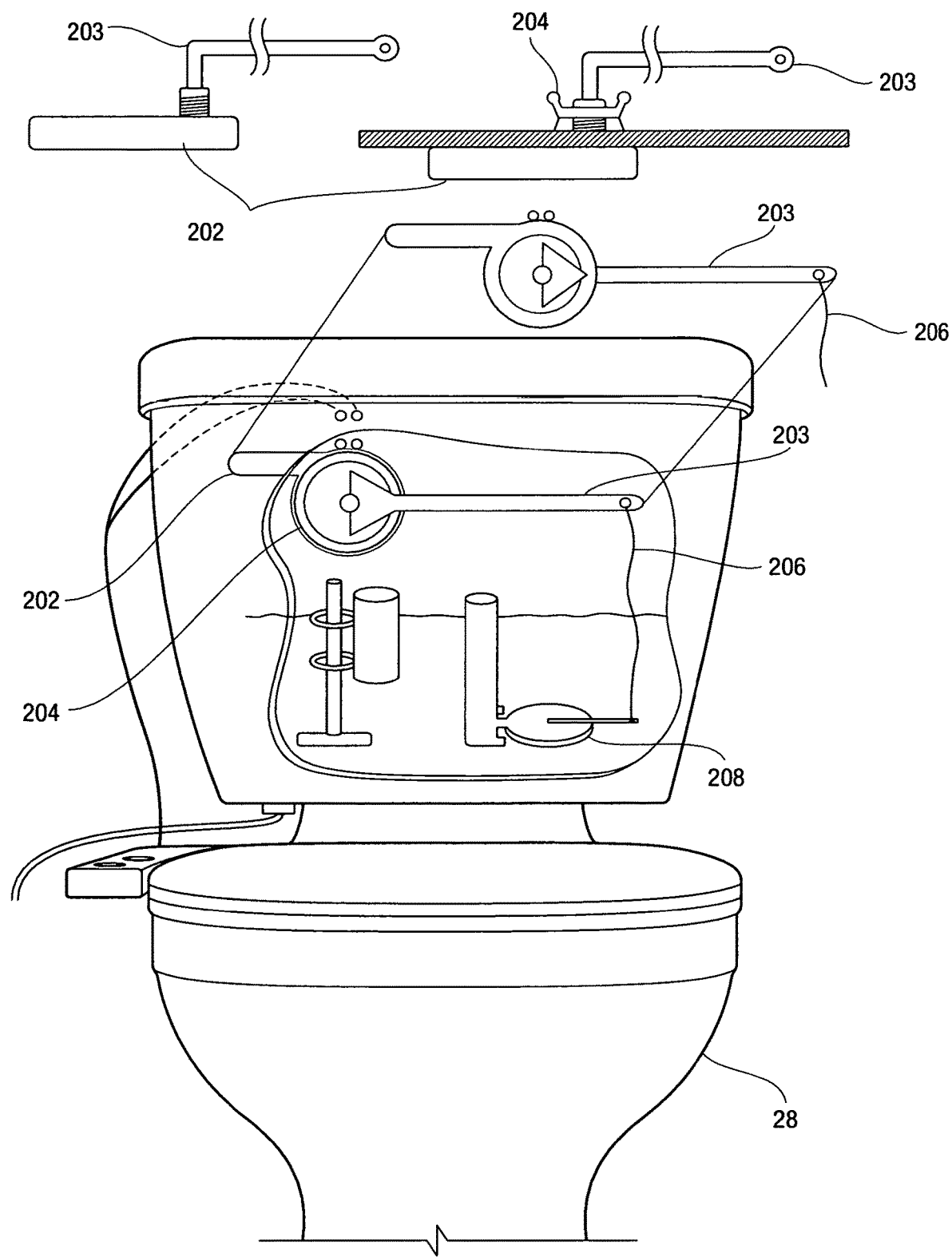
FIG. 22 shows a perspective view, including cut-away perspective view, of selected portions of the smart toilet system of the present disclosure, as well as multiple top plan view and side elevation views of certain selected components of the present disclosure.

FIG. 22 shows the automated flush mechanism of the smart toilet system of FIG. 1 wherein the automated flush mechanism has an electric or mechanical switch 4 along with the standard toilet handle 2, rod 3, pull chain 6, and flapper 8.

Figure 23:
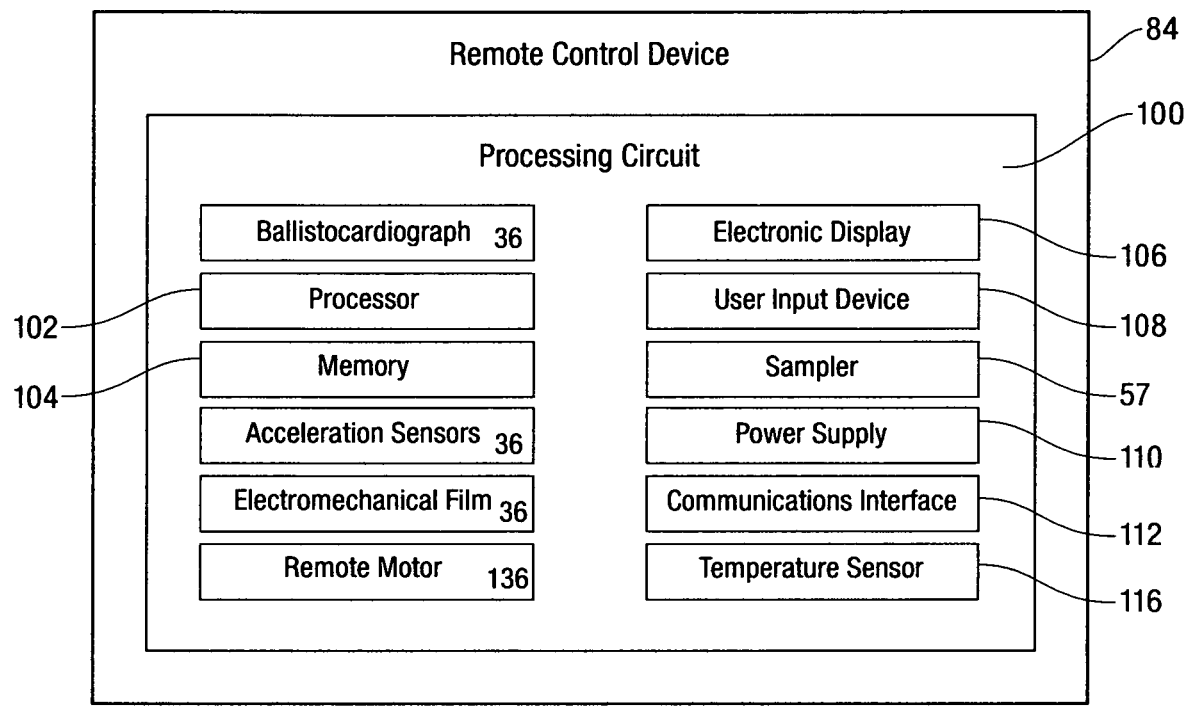
FIG. 23 shows a block diagram of the capabilities and functions of a remote control and/or a control box of the present disclosure.

FIG. 23 shows a block diagram of the remote control 84, illustrating its capabilities and functions. See FIG. 18 and FIG. 21.

Figure 24:
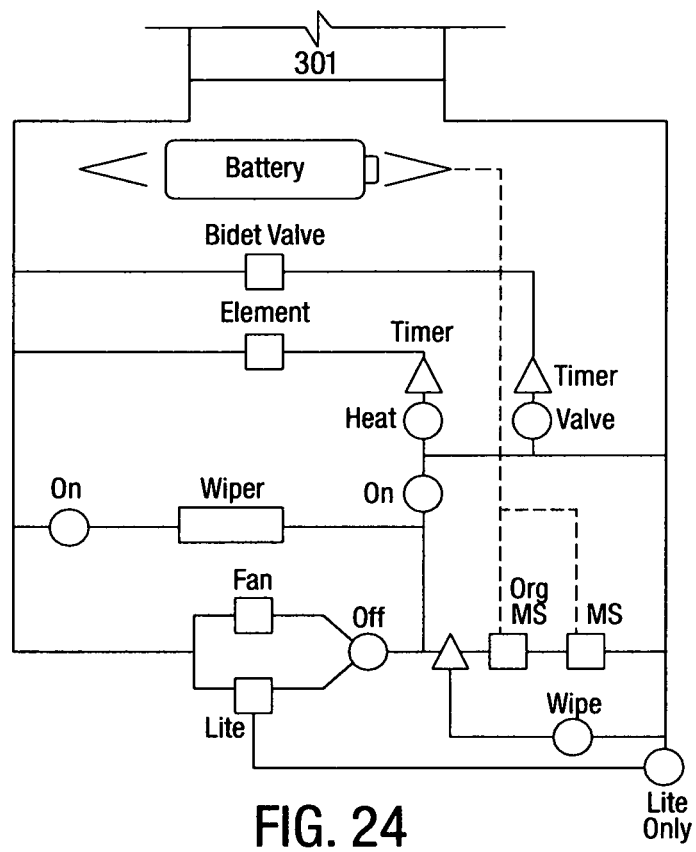
FIG. 24 shows a flow chart diagram of the capabilities and functions of selected portions of the smart toilet system of the present disclosure.

FIG. 24 shows a flow chart diagram of the capabilities and functions of the UAC processing-unit 301 as it communicates with the processing unit of the ORG 20 and the bidet. See FIG. 5.

Figure 25:
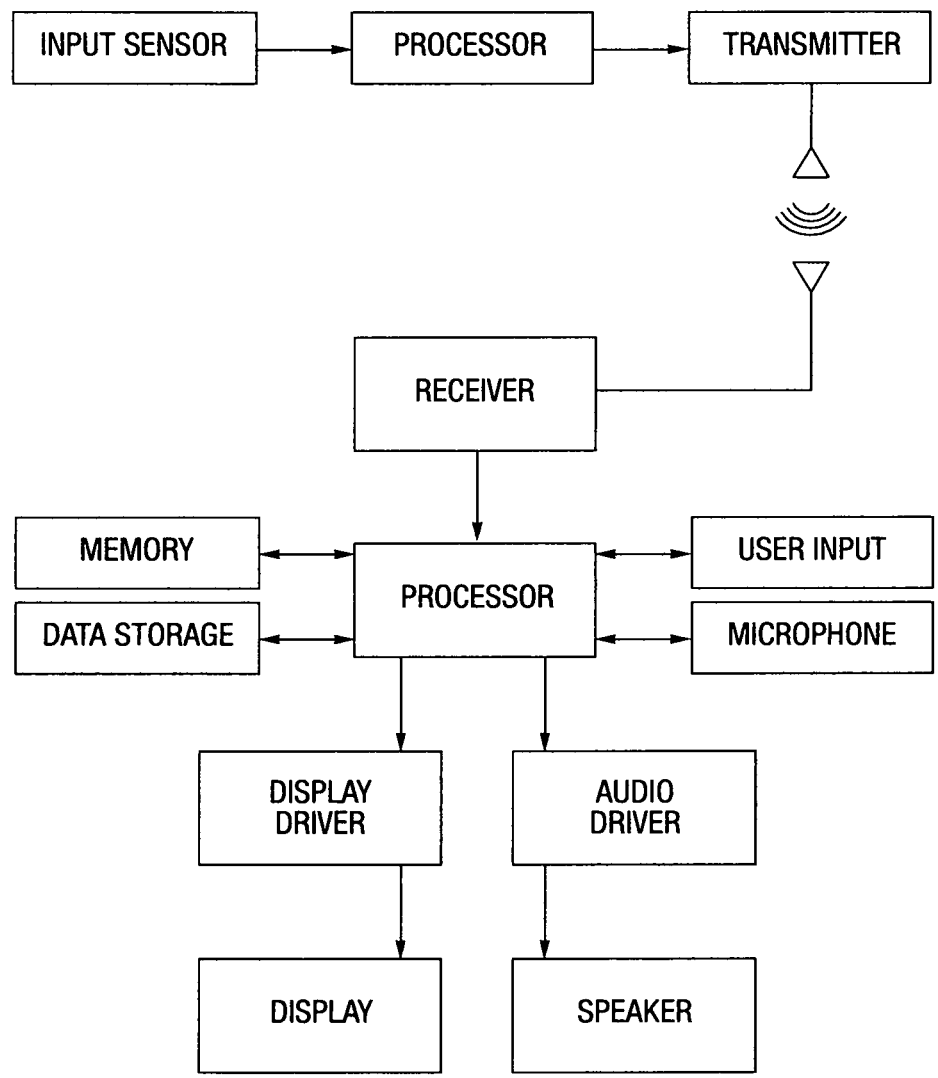
FIG. 25 shows a flow chart diagram of the capabilities and functions of selected portions of the smart toilet system of the present disclosure.

FIG. 25 shows a flow chart diagram of the ORG-processing-unit 300 unit of the ORG 20, wherein the processing unit collects data from the various aspects of the smart toilet system 10 connected to the ORG 20 and provides the data collected to the control box 160 for further processing. The upper portion of FIG. 25 shows the transmitter part as a schematic of a component for remote control of the ORG 20, which may be implemented as a remote control 84. The lower portion of FIG. 25 shows the bottom receiver processor part, which may be implemented as a control box 160.

Figure 26:
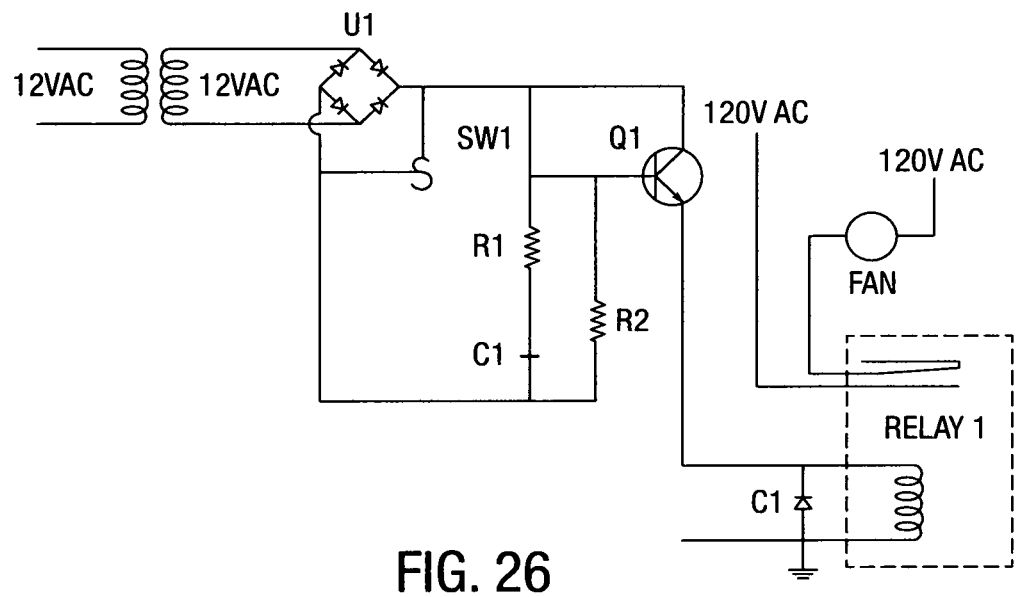
FIG. 26 shows a circuit diagram of selected portions of the smart toilet system of the present disclosure.

FIG. 26 shows a circuit diagram of the bathroom ceiling fan boxes 72 with a transformer.

Figure 27:
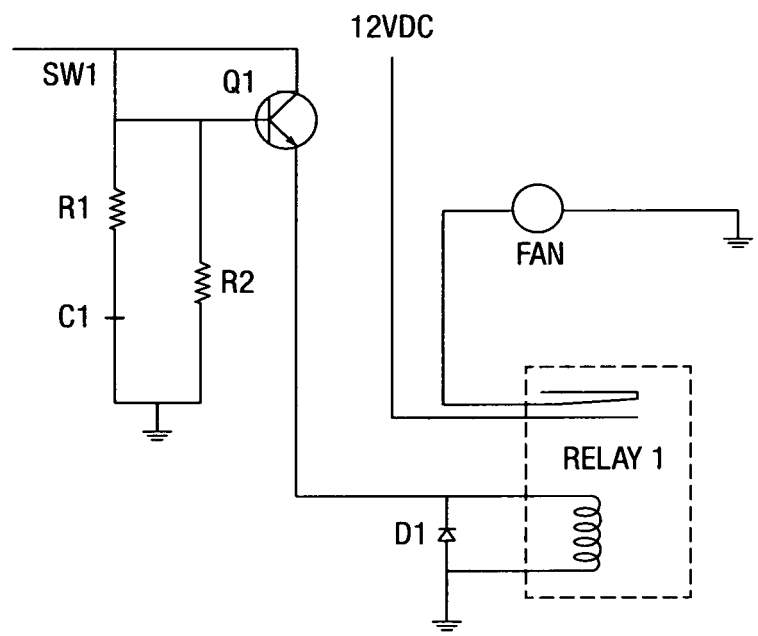
FIG. 27 shows a circuit diagram of selected portions of the smart toilet system of the present disclosure.

FIG. 27 shows a circuit diagram of the vessel 51 heater and water valve switch.

FIG. 28 shows a block diagram of the electrical components of the plumbing fixture of the smart toilet system of FIG. 1. FIG. 28 shows the processing circuit, data connections, remote receiver, control panel, lighting element, and sensor as they communicate within the smart toilet system 10.

Some of the components enclosed within or supported by the ORG 20 are in communication with a control box and processing system. In another embodiment, the components supported by the ORG 20 may communicate directly with the processing circuit 140 of the control box 160 through the ORG-processing-unit 300 of the ORG 20.

One embodiment of the basic structure of a smart toilet system 10 will now be described with reference to FIGS. 1-3. Referring to FIG. 1, one embodiment of the smart toilet system 10 comprises a toilet bowl 30, a toilet tank 28, a toilet seat 26, an ORG 20, and a toilet seat cover 24. As shown in FIG. 1, FIG. 2A, and FIG. 2B, the ORG 20 supports or encloses the primary components that support various subsystems of the smart toilet system 10. The ORG 20 may also comprise a vacuuming system 114 configured to remove odors from the toilet bowl 30, to a bathroom exhaust fan 12, and comprise a processor 142 and processing circuit 140, including a control box 160 as depicted in FIGS. 15-16B.

Referring to FIGS. 1-3 and FIG. 22, in some embodiments, the smart toilet system 10 functions as a toilet, or on or with a toilet, using the fluid to flush, rinse, or otherwise clean the toilet bowl 30. The smart toilet system 10 may provide a variety of automatic flushing options, such as but not limited to user voice controlled, weight or motion sensor automated flushing, configured to carry out the flushing process.

Still referring now to FIGS. 1-3, in the described embodiment, the ORG 20 may be situated between the toilet seat 26 and the toilet bowl lip 38 of the toilet bowl 30. The ORG 20 may lay beneath the toilet seat 26 and adjacent to the rear end of the toilet bowl 30. The ORG 20 may be supported by the bottom surface of the toilet seat 26 by permanent means (e.g., bolts, screws, adhesives, resin, glue) or removable placement (e.g., adhesives, hook-and-loop fasteners). Further, in another embodiment, the ORG 20 may be remote to the smart toilet system 10.

Further, as depicted in FIGS. 1-2B and FIG. 9, the ORG 20 may contain top and bottom surfaces. The top and bottom surfaces of the ORG 20 may be a unitary structure or removably joined together. In one embodiment, the material of the housing 60 of ORG 20 may be flexible or rigid and be made of standard building, construction, or plumbing material known in the art. Additionally, the ORG 20 may or may not have hollow regions within the body of the ORG 20 as depicted in FIG. 9. In some embodiments, ORG 20 may be a single shell or may include multiple shells.

Referring to FIGS. 2A-2B, and FIG. 5, the ORG 20 may be shaped in a "U" or an "O" configuration. Alternatively, the ORG 20 may be designed to fit the shape of the toilet seat 26 or toilet bowl 30. The ORG 20 may support a plumbing connection tee tubing 70 (as depicted in FIG. 15), a plumbing connection elbow tubing 19 (depicted in FIG. 15), and/or comprise a plurality of front odor openings 16 for ventilation (depicted in FIG. 7 and FIG. 8).

An embodiment of the ORG 20 is shown in FIG. 2A. The ORG 20 may function with or without a top and bottom surface. Now turning to FIGS. 4-6 for a further description of the ORG 20.

Referring now to the embodiment shown in FIGS. 4-6, the front end of the ORG 20 may be located on the toilet seat. A front end of the ORG 20 may be affixed to the toilet seat 26 or toilet bowl 30. As depicted in FIG. 3 and FIG. 4, in one embodiment all or a portion of the ORG 20 may be located underneath the toilet seat 26. Further, as depicted in FIG. 4, the ORG 20 may house or support a plurality of motion sensors 44, a plurality of lighting elements 56, a plurality of body weight sensors 46, a plurality of impedance photoplethysmography sensors 36 (not shown), a plurality of infrared lights 32, and a sticker attachment 35 (specifically a sticker attachment 35 which may comprise the smooth flush finish 31, the plurality of infrared lights 32, the glucose monitor 33, and the plurality of impedance photoplethysmography sensors 36), of printed electronics, lights, and electrode designs with AI to perform Transdermal Optical Imaging (TOI) to reflect deep into the skin, up to 5 inches, for digital biomarkers including but not limited to heart rate, electrocardiogram, and more; collectively a plurality of sensors, and wherein the plurality of sensors is in electrical communication with the ORG processing-unit 300 of the ORG 20. The infrared lights 32 may be infrared or nearinfrared lights, or other apparatus to generate electromagnetic radiation or light in the vicinity of the infrared zone of the electromagnetic spectrum. The impedance photoplethysmography sensors 36 may be used for measuring body mass index (BMI), blood volume, ballistocardiography, or other measures of health or body function that may be measured with impedance photoplethysmography. The ORG-processing-unit 300 of the ORG 20 may communicate a plurality of data and input received from the ORG 20 and the foregoing sensors to the processor 142 of the control box 160.

For example, the plurality of impedance photoplethysmography sensors 36 receive an input signal and communicates that signal to the processor 142 through the ORG-processing-unit 300 of the ORG 20, which interprets the signal and initiates one or more control actions. For example, the ORG-processing-unit 300 may cause usable information from the impedance photoplethysmography sensors 36 to be displayed or announced via a speaker or store the information on an external server (e.g., an external cloud server) or other memory device. The processor 142 may comprise the ORG-processing-unit 300.

Referring to FIGS. 4-5, the rear end of the ORG 20 may be supported by the top of the toilet bowl 30 or the bottom of the toilet seat 26. As best shown in FIG. 20, the smart toilet system 10 may comprise a rear bidet sprayer head 40, a user arm controller 34, a toilet user's wiper system 52, and an odor removal system through the VET 18. In one embodiment, the user arm controller 34 can be located on the left of the toilet bowl 30 as illustrated in FIG. 5 at the right (or left) side of the ORG at rear odor openings 17 of the ORG 20; the rear bidet sprayer head 40, wiper system for toilet user 52, and odor removal aspects are located beneath the toilet seat 26 as shown in FIG. 3. In another embodiment, the user arm controller 34 can be located on the right side of the toilet bowl 30 at the right side of the ORG 20 at rear odor openings 17. The user arm controller 34 contains the UAC-processing-unit 301 capable of providing input from the user arm controller 34 to the ORG-processing unit 300 of the ORG 20. The processor 142 may comprise the UAC-processing unit 301. The ORG 20, as shown in FIG. 5, supports electrical or electronic components that communicate with the user arm controller 34 via the control box 160 to allow the bidet water heating capabilities of the rear bidet sprayer head 40, wherein the ORG 20 supports circuitry through the ORG-processing-unit 300 of the ORG 20 that communicates with a vessel 51 via the control box 160 as illustrated in FIG. 20. The vessel 51 may be temperature-controlled and/or insulated, and may be used to regulate water temperature and/or supply fluids that is at a comfortable temperature to the rear bidet sprayer head 40 and/or to the front bidet sprayer head 40a.

As depicted in FIGS. 8-9, the ORG 20 may comprise a housing 60, wherein the housing 60 may comprise a top surface, a bottom surface, and a plurality of side surfaces. The housing 60 may comprise top, bottom, and sides that may be separate detachable and cleanable pieces. These detachable pieces of the housing 60 may be supportable by removable means (e.g., adhesives or hook and-loop fasteners). In another embodiment, the housing 60 may be formed as a unitary piece having an access point to the inner components. The housing 60 may be of standard building materials including metal, wood, resin, natural or synthetic polymers (e.g., rubbers, plastic, resin), or other materials now known or later invented.

As best illustrated by FIG. 25, in operation, sensors supported by or housed within the ORG 20 communicate with the processing circuitry through the ORG processing-unit 300 of the ORG 20 (depicted in FIG. 7). For example, the impedance photoplethysmography sensors 36 receives an input signal once a user sits on the toilet. The processing system processes the input signal and initiates certain actions or controls such as transmitting the processed signal to a display device or audio sound device, such as, but not limited to, a speaker.

As depicted in the embodiment shown in FIGS. 4-6 and FIG. 12, the ORG 20 supports a plurality of lighting elements 56, as best seen in the exemplary embodiment of FIG. 10A. One embodiment of the plurality of lighting elements 56 comprises light emitting diodes (LEDs), though as will be apparent to one of skill in the art, the plurality of lighting elements 56 may comprise any type or multiple types of individual lights or strip lights now known or later invented.

The lighting elements 56 shown in FIG. 12 are capable of being automatically activated or de-activated, i.e. turned on or off, based on an input to at least one of the one or more of the motion sensors 44. At the detection of motion by the motion sensors 44, the lighting elements 56 will turn on. Referring to FIG. 21 and FIG. 23, the lighting elements 56 may be turned on or off by a remote control 84, wherein the remote control 84 may comprise a mechanical component, an electronic component, and/or a computer interface, including but not limited to a computer application which may be run on any computer or mobile computer, including but not limited to a laptop, desktop, computer built in to a home or room, smart phone, tablet, phablet, smart watch, or other computing device now known or later invented. The remote control 84 may be implemented as one or more software applications built to run on any of the foregoing computing devices. The remote control 84, implemented as software, may be used to store, log, track, and/or share information related to diagnosis or treatment of medical conditions or diseases, including but not limited to COVID-19 and comorbidities for COVID-19. The remote control 84, implemented as software, may implement self-reporting features, may implement artificial intelligence and/or Machine Learning (AI/ML) capabilities, and/or may collect vital information from the user of the smart toilet system 10 and the remote control 84, and thus may be used to store, log, track, and/or share information related to diagnosis or treatment of medical conditions or diseases, including but not limited to COVID-19 and comorbidities for COVID-19. The lighting elements 56 can be turned on or off by the remote control 84 through communication between the remote control 84 and the control box 160; the control box 160 provides the input to the lighting elements 56 via the processor 142 to turn the lighting elements 56 either on or off.

Referring to FIG. 10A, there may be a plurality of motion sensors 44, as supported by the ORG 20. The motion sensors 44 are capable of providing feedback to the control box 160 that signals various parts of the smart toilet system 10 to turn on or off. In an embodiment with more than one in the plurality of motion sensors 44, as depicted in FIG. 10B, the motion sensors 44, located at the edge of the ORG 20, are placed to allow the ORG 20 to lay balanced on the toilet seat 26 and toilet bowl 30. Additionally, in another embodiment, there may be a plurality of motion sensors 44 located at a plurality of tips of the ORG 20 of FIG. 10B to allow for multiple angles of motion detection.

Referring now to FIG. 1, FIG. 3 and FIG. 5, the smart toilet system 10 may include circuitry permitting the motion sensors 44 to communicate with the body weight sensors 46, infrared lights 32, and impedance photoplethysmography sensors 36 in order to turn them on or off, i.e., they may be activated or de-activated. The motion sensors 44 as depicted in the embodiment shown in FIG. 4 points towards the outer side of the smart toilet system 10 and is capable of detecting motion surrounding the vicinity of the smart toilet system 10. The motion sensors 44 communicate with the control box 160 through the ORG 20 to provide the automatic on and off functionalities of body weight sensors 46, infrared lights 32, and impedance photoplethysmography sensors 36. The motion sensors 44, the body weight sensors 46, and the lighting elements 56 may be connected to power and data signal transmission, with reference to FIG. 6.

Referring to FIG. 13, in the embodiment shown, the plurality of impedance photoplethysmography sensors 36; the plurality of infrared lights 32; at least one (electrode) electromechanical film (EMFI) sensors, at least one piezoelectric tape sensor, at least one metallic film sensor, and at least one graphite based sensor, which may comprise a low-cost, printed, graphene nanocomposite strain sensor (collectively the electrodes 49); and a plurality of temperature sensors 116 are attached to a smooth flush finish 31 on that is fitted at the top of the toilet seat 26 with the same diameter, shape, of the toilet seat 26. The smooth flush finish 31 is constructed using standard construction material as used in the art. In another embodiment, the impedance photoplethysmography sensors 36, infrared lights 32 and the plurality of temperature sensors 116 are attached to a smooth flush finish 31 on that is capable of covering part of the surface of the top of the toilet seat 26. The smooth flush finish 31 comprises at least one of the electrodes 49 (e.g., acoustic transducers) illustrated in FIG. 13. In an embodiment where there is more than one of the electrodes 49 as depicted in FIG. 13, the electrodes 49 will be placed at equal distribution and designs around the smooth flush finish 31.

In an embodiment, the acceleration sensors (e.g., ADXL2020 and MXA25004) in FIG. 25 communicates with the ORG-processing-unit 300 (circuitry of the ORG processing-unit depicted in FIG. 24) of the ORG 20 as depicted in FIG. 7, which then communicates the data collected to the processor 142 of the control box 160. The acceleration sensors, of FIG. 25, provides a system for remote monitoring of the user through an integrated scale, which may be piezoelectric as shown in FIG. 11, wherein the integrated scale is capable of measuring body weight of user to determine and recognize a specific designated user. The foregoing acceleration sensors may be incorporated with the plurality of body weight sensors 46.

Referring to FIG. 13, in an embodiment, the electrodes 49 of the smooth flush finish 31 transmits sound waves back and forth by electrical echo signals in an upward direction from the toilet seat 26. The electrodes 49 of the smooth flush finish 31 ultrasonically measures and identifies the weighed user. Data collected for the identification of the weighted user is collected in the ORG-processing-unit 300 of the ORG 20, which is then transmitted to the processor 142 of the control box 160, where it is then communicated to the remote control 84, smart phone, or external server (e.g., cloud-based server). In another embodiment, if there is a previous identification available, the transceiver will automatically transmit the body weight, body muscle/fat percentages, BMI, blood pressure, respiratory rate, water content ratio, heart rate, collected bowel activity, bladder volume, inner physiological bone structure/measurements, and spinal differentiations through communication with the ORG-processing-unit 300 of the ORG 20, which can directly communicate the data to a multiplexer via a communication link displayed in the control console unit and then stored in a remote monitoring device (e.g. external server or smartphone or other electronic device).

Still referring to FIG. 13, the sound waves of electrodes 49 of the smooth flush finish 31's the pulse echo (EKO) sounds waves or other frequency of waves that are used in the art that communicates with motion extractors, motion filters, digital signal processing systems, and analogy-to-digital converters to obtain pulse wave volume, ballistocardiographic (BCG) and pulse transmit time data. In the same embodiment, the EMFI, BCG with the impedance photoplethysmography sensors 36 collected by the processing unit of the ORG 20, transmitted to the control box 160, and then communicated to the remote control 84, smart phone or external server (e.g., cloud-based server) where it can be read by the user.

Referring to FIG. 14, in one embodiment, the toilet seat cover 24 supports infrared lights 32 or lights of other wavelengths. The infrared lights 32 may be located on the inner side, bottom surface of the toilet seat cover 24. One or more of the infrared lights 32 may be placed flushed at an upper surface of the toilet seat cover 24. In another embodiment, a bullseye-arrangement intense pulse light 69 may be disposed at or approximately at a top and center position of the toilet seat cover 24, advantageously to be used when in a closed position. The intense pulse light for hair removal, the infrared coagulation skin refurbisher LED may be placed on the top side or the upper surface, of the toilet seat cover 24 or of the toilet seat 26. In another embodiment, the infrared lights 32 may be placed under or on the upper surface of the toilet seat 26. At the detection of the motion of a user by motion sensors 44, and/or by the detection of a seated user by body weight sensors 46, the infrared lights 32 and/or the bullseye-arrangement intense pulse light 69 will turn on; at the loss of detection of motion by motion sensors 44 or of the seated user by body weight sensors 46, the infrared lights 32 and/or the bullseye arrangement intense pulse light 69 will turn off. Also infrared lights 32 may be turned on or off by remote control 84 or through a smart phone's application. The infrared lights 32 can be turned on or off by remote access (i.e., remote control 84 or through a smart phone's application) through communication between the remote access and the control box 160; the control box 160 provides the input to the infrared lights 32 via the ORG 20 turn the infrared lights 32 either on or off. The glucose monitor 33 and impedance photoplethysmography sensors 36 may be disposed on the toilet seat cover 24.

Still referring to FIG. 14, in one embodiment, the toilet seat cover 24 supports attached impedance photoplethysmography sensors 36 and a glucose monitor 33 located on the outermost edge, near the tip of the toilet seat cover 24.

In an alternate embodiment, the infrared lights 32 can be adapted to detect body temperature, in combination with or in lieu of the temperature sensors 116.

Another embodiment may contain infrared lights 32 at the toilet seat 26 of FIG. 1 One or more of the plurality of infrared lights 32 may be placed flush at an upper surface and/or an inner side of the toilet seat 26. The infrared lights 32 may be activated for seated therapy treatment.

Referring to FIG. 13, at least one of the plurality of temperature sensors 116 is present on the toilet seat 26 and/or on the toilet seat cover 24. The plurality of temperature sensors 116 use infrared lights to detect variances in temperature. Data from the plurality of temperature sensors 116 is processed in the ORG processing-unit 300 of the ORG 20. Information gathered from the temperature sensors 116 may be used to store, log, track, and/or share information related to diagnosis or treatment of medical conditions or diseases, including but not limited to COVID-19 and comorbidities for COVID-19.

In the same embodiment, as shown in FIG. 13, impedance photoplethysmography sensors 36 may be placed on the top of the toilet seat 26. Alternatively, the smart toilet system may be configured to comprise one or more of an electronic blood pressure cuff-defibrillator-electrode 54 as depicted in FIG. 3.

Referring now to FIG. 2A, FIG. 9, FIG. 15, FIG. 16A, and FIG. 16B, the smart toilet system 10 may remove odor through the ORG 20, the fan deodorizer 48, the vacuuming system 114, and the bathroom exhaust fan 12. In the embodiment described, the vacuuming system 114 sensors and controls attach at the rear end of the ORG 20. The ventilation system supporting the vacuuming system 114 as described herein contains vacuum exhaust tubing. The odor collected within the ORG 20 can flow out from the ORG 20 at rear odor openings 17, and flow into and/or through the VET 18. The ORG 20 is connected to the VET 18 through the VET arm 62, wherein the VET arm 62 is connected to the plumbing connection tee tubing 70 as shown in FIG. 3 and FIG. 9 at the rear odor openings 17. As shown in FIG. 7 and FIG. 8, there is a plurality of front odor openings 16 and a plurality of rear odor openings 17. In an embodiment, rear odor openings 17 comprise an attachment slot for the VET arm 62 or the fan deodorizer 48 or a possible cap. In this embodiment, the plurality of front odor openings 16 and the plurality of rear odor openings 17 of the housing 60 of the ORG 20 allows possible gas (e.g., air and odors) to enter into the vacuuming system 114 from the ORG 20. The openings, which may also be referred to in the present disclosure as "holes", of the ORG 20 may be present through the inner or outer sides of the ORG 20 for the purpose of collecting the odor surrounding or within the toilet bowl 30 or the area surrounding the toilet bowl 30. The odor from the plurality of front odor openings 16 of the ORG 20 will travel to the VET 18 and optionally through the control box 160 and will eventually be sucked out of the room by the bathroom exhaust fan 12. There will be one or more in-apparatus fans 14 throughout the VET 18 to promote or enhance the strength of the vacuuming of the odors. As depicted in FIG. 7, in another embodiment, odor could be removed from rear odor openings 17 if no VET arm is connected. As depicted in FIG. 7, in another embodiment, the cap is used to cover rear odor openings 17 if no VET arm is connected. Further, in an alternate embodiment odor could be removed from rear odor openings 17 with a fan deodorizer 48 (described below in more detail).

Referring to FIG. 1 and FIG. 9, the vacuuming system 114 communicates with the processor 142 via the processing circuit 140 to provide odor removal. The control box 160 as depicted in FIG. 20 communicates with the in-apparatus fans 14 and bathroom exhaust fan 12 based on the input received by the remote control 84. The remote control 84 has an on/off switch or similar feature that allows the user to turn on and off the vacuuming system 114.

In another embodiment, the rear end of the ORG 20, as depicted in FIG. 2A, may support or house the controls for a fan deodorizer 48 in the place of the bathroom exhaust fan 12 at rear odor openings 17. The fan deodorizer 48 communicates with the ORG 20 through the ORG-processing-unit 300 to be turned on either by the motion sensors 44 for automatic functionalities as triggered by the motion sensors 44, by the remote control 84, or by the body weight sensors 46.

Referring to FIGS. 16A-16B, the VET 18 may connect with the bathroom exhaust fan 12 at an opening of the bathroom fan cover 74 or the base of the bathroom ceiling fan boxes 72. The opening of the bathroom fan cover 74 or bathroom exhaust fan 12 is wide enough to cover either the VET 18 opening or an in apparatus fan 14. The bathroom exhaust fan 12 can be a standard bathroom fan as known in the art, attached to a base to form a smart ceiling fan cover.

In one embodiment, the bottom of the VET 18, may contain a VET trap 22, as depicted in FIG. 1 and FIG. 2B. The VET trap 22 may be removable and replaceable. The VET trap 22 may be a removable cap as shown in FIG. 15. The VET trap 22 attaches at the opposite end of the VET 18 that connects to the bathroom exhaust fan 12. Further, the VET trap 22 can be made of the same material as the VET 18, or another similar material used in the art. The VET trap 22 can attach to the VET 18 as an inserting draw or by pulling the VET trap 22 downwards from the VET 18.

As depicted in FIG. 17, the in-apparatus fans 14 comprise a plurality of fan-blades 78, at least one open hole 82 through the frame 76 to allow the wires to pass through without tangles, and a region for the air to flow through. The in-apparatus fans 14 can operate by electrical means (e.g., operate with an electrical connection and optionally a motor) or passively with the plurality of fan-blades 78. The in apparatus fans 14 operating electrically communicates with the remote control 84 via the control box 160 to be turned on and off. Further, the in-apparatus fans 14 may be turned on/off individually or jointly with the rest of the vacuuming system 114. The in-apparatus fans 14 can be situated to fit within the inner lining of the VET 18, linked to two portions of the VET 18, be nestled at the top of the control box 160, or linked to a portion between the VET 18 and the control box 160. The in-apparatus fans 14 may be constructed from metal or plastic materials commonly used for building fans. The frame 76 of the in-apparatus fans 14 may be in the box be sharp at the edges or may be rounded. The plurality of fan-blades 78 may move in a counterclockwise or clockwise direction. And optionally, the in apparatus fans 14 may contain deodorizer capabilities.

In another embodiment, the in-apparatus fans 14 of FIG. 17 may be battery powered.

Figure 29:
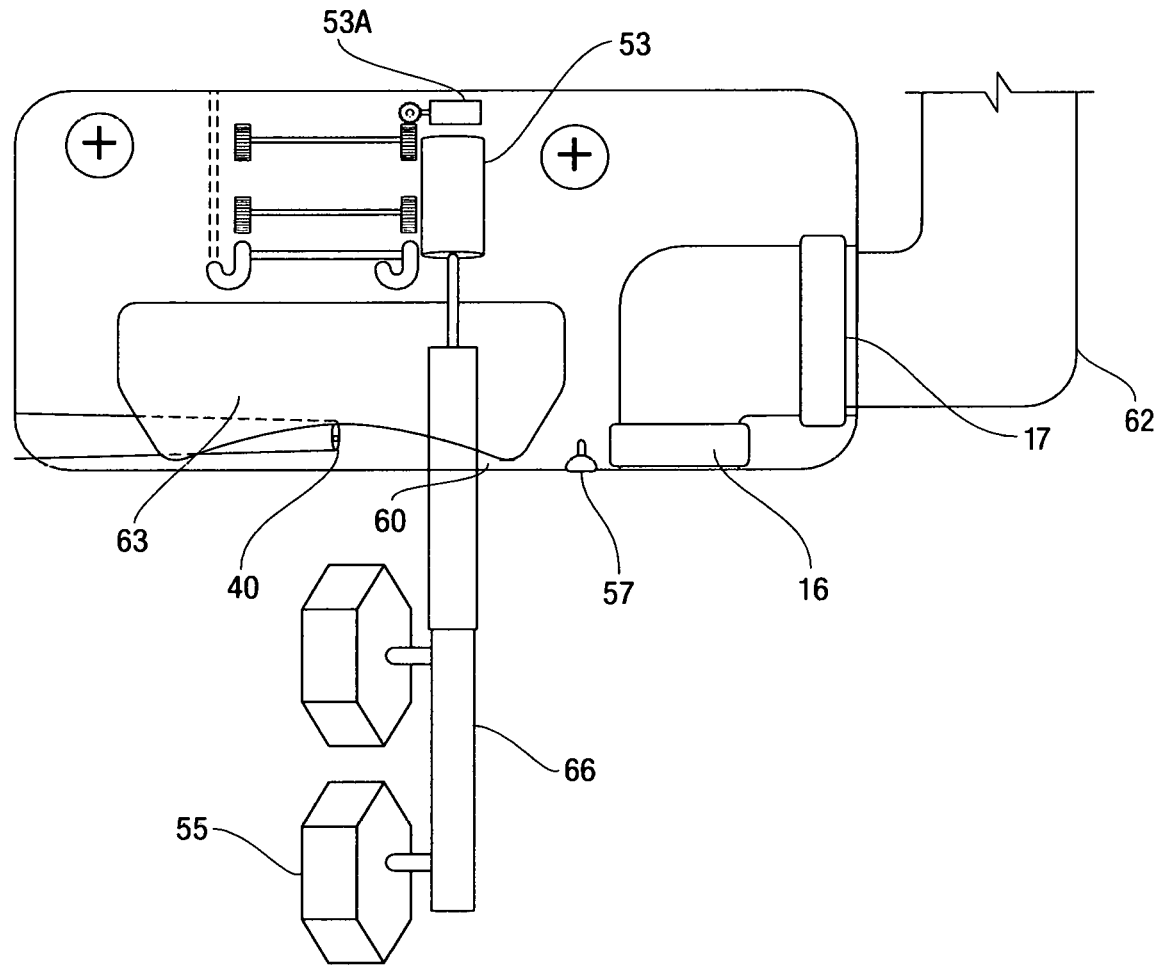
FIG. 29 shows a partial top plan view and partial top plan cut-away view of selected portions of the smart toilet system of the present disclosure.
Figure 30:
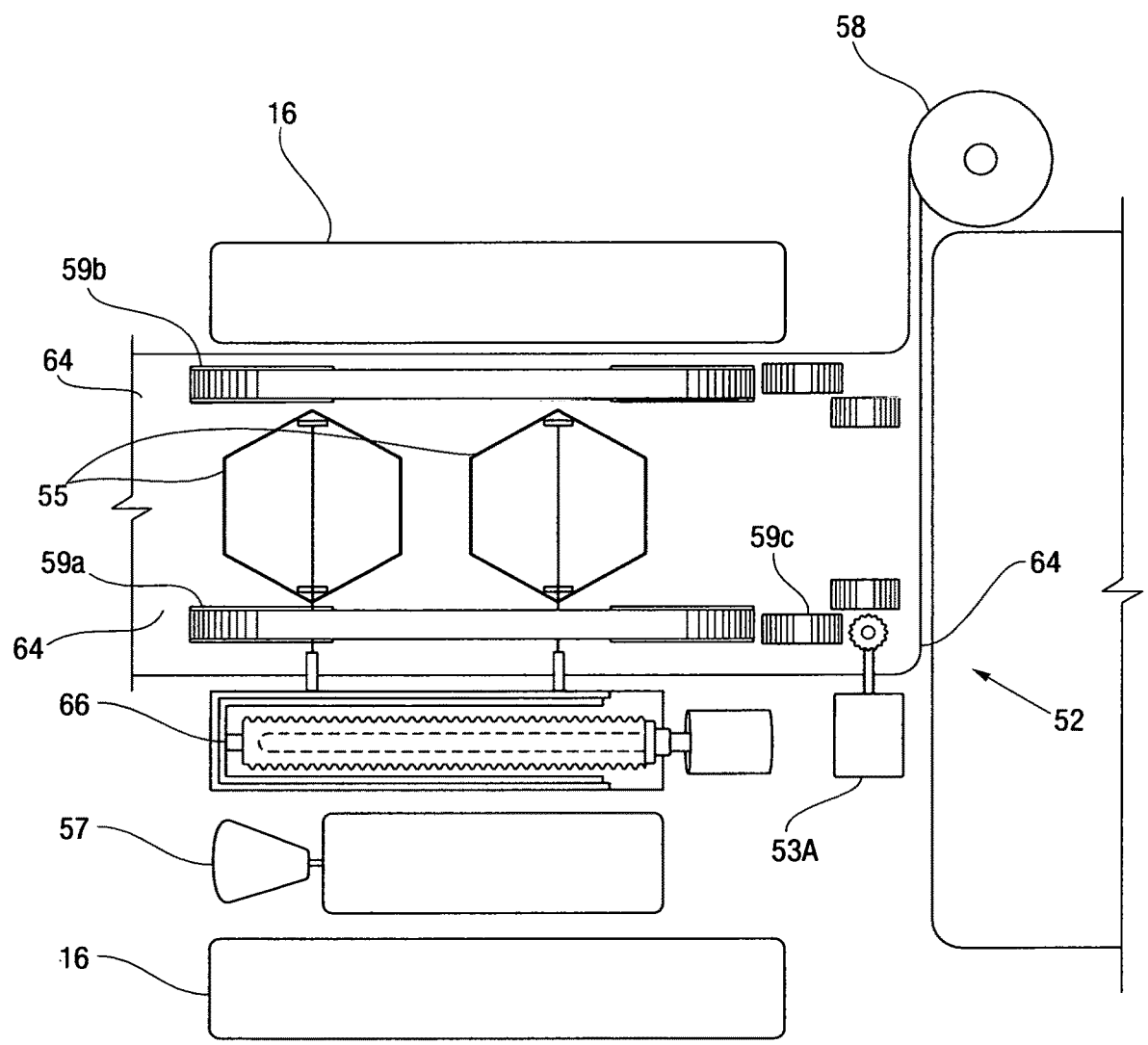
FIG. 30 shows a partial top plan view and partial top plan cut-away view of selected portions of the smart toilet system of the present disclosure.
Figure 31A:
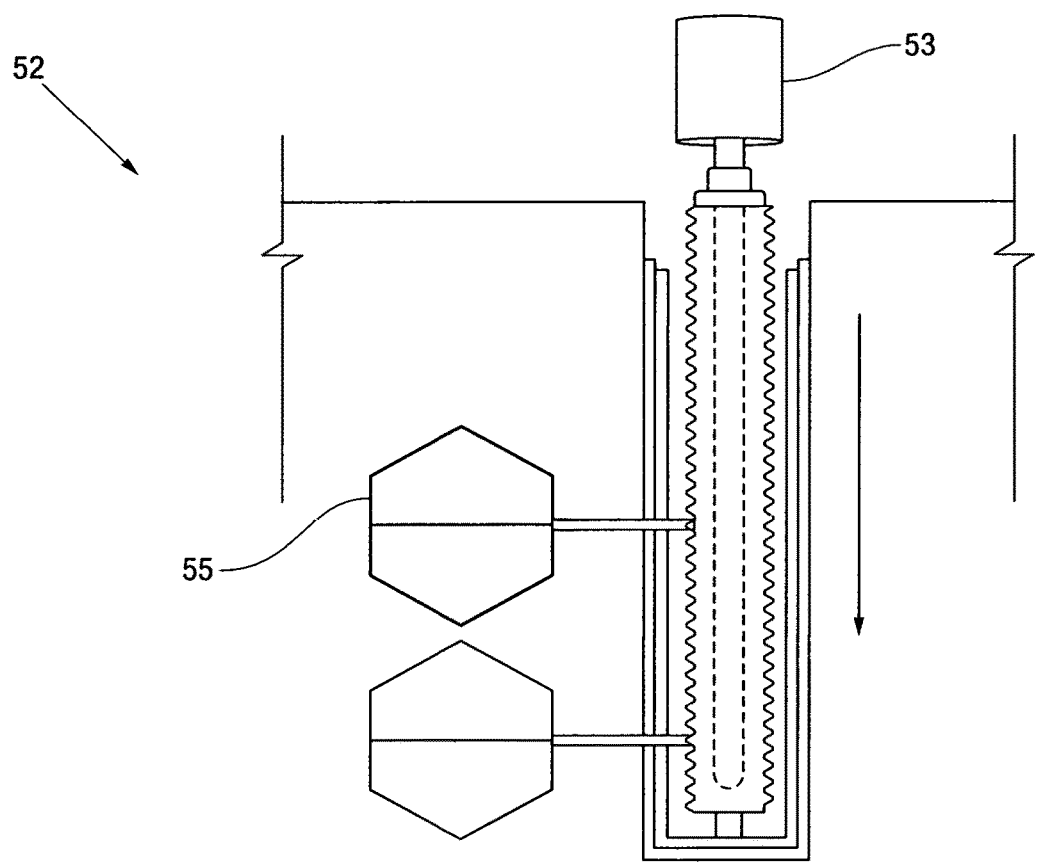
FIG. 31A shows a cut-away partial top plan view of selected portions of the smart toilet system of the present disclosure.
Figure 31B:
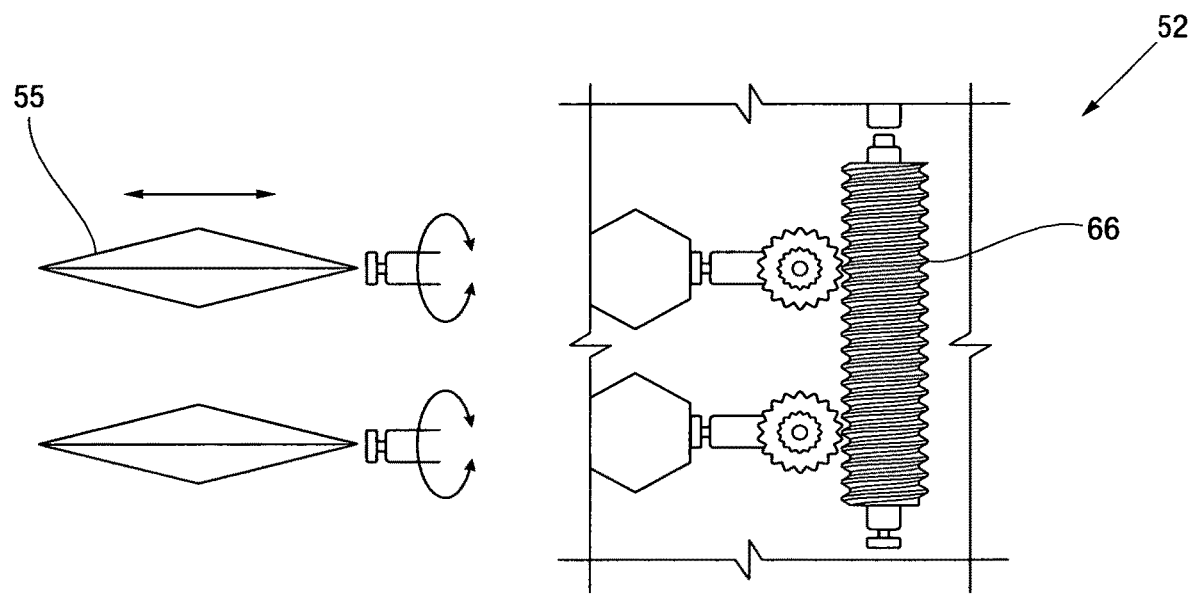
FIG. 31B shows a cut-away partial top plan view of selected portions of the smart toilet system of the present disclosure.

Referring now to FIG. 3 FIG. 7, FIG. 29, FIG. 30, FIG. 31A, FIG. 31B, and FIGS. 32-36, the ORG 20 may further comprise, or may contain, a toilet user's wiper system 52. The toilet user's wiper system 52 of the ORG 20 contains a tissue roll feeder 58 (depicted in FIG. 4) and a motorized hygiene wiper 53 (depicted in FIG. 7), and the toilet user's wiper system 52 may be partially or fully automated. The tissue roll feeder 58 is capable of shielding or protecting any toilet paper 64 that is still on the tissue roll feeder 58. As depicted in FIGS. 29-36, standard toilet paper is mechanically rolled onto the cylindrical balls 55 of the motorized hygiene wiper 53, wherein the toilet paper is wrapped around the top and bottom of the cylindrical balls 55. The tissue paper on the cylindrical balls 55 are capable of extending outwards into the toilet bowl 30 to wiper clean of the user as depicted in FIG. 29 through a toilet-paper-feeder port 63 of the ORG, as depicted in FIG. 7 and FIG. 8 and FIG. 9. In one embodiment, as depicted in FIG. 31A and FIG. 31B, the cylindrical balls 55 are capable of collapsing to aid with discharging used tissue; the mechanical structure is capable of tilting the cylindrical balls 55 to allow the used toilet paper to fall into the toilet bowl 30. As depicted in FIG. 30, the cylindrical balls 55 are capable of re-expanding in order to be re-wrapped with fresh toilet paper in the housing 60 of the ORG 20. In some aspects of the present disclosure, there may be a second wiper motor 53a, used for extension.

Figure 34:
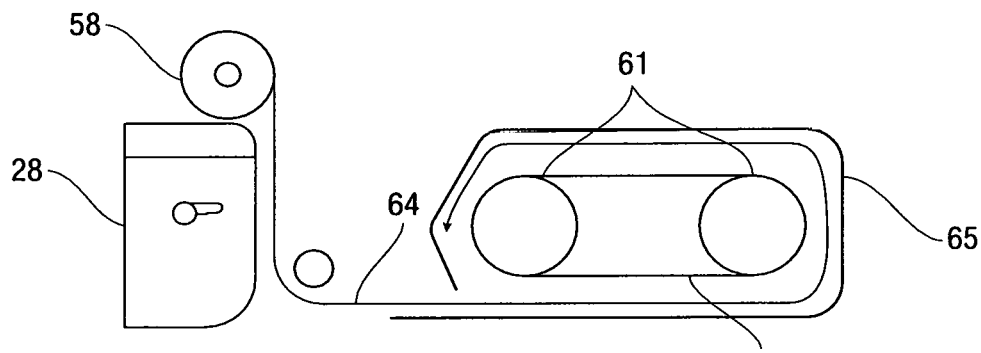
FIG. 34 shows a partial side plan view of an aspect of the smart toilet system of the present disclosure.
Figure 35:
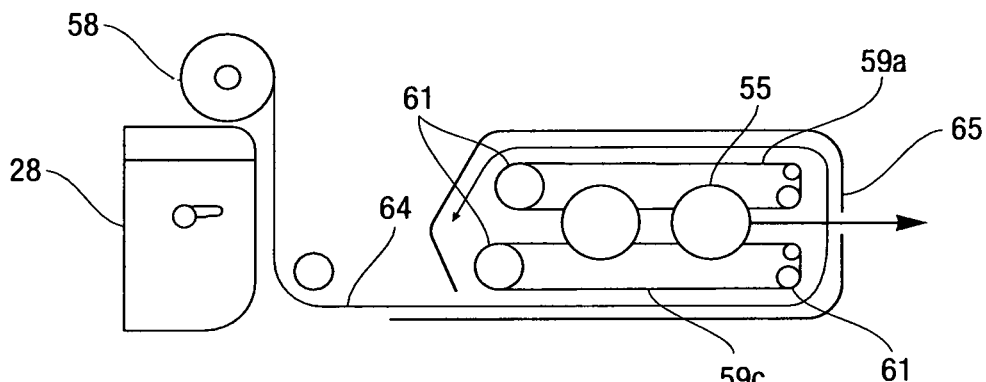
FIG. 35 shows a partial side plan view of an aspect of the smart toilet system of the present disclosure.
Figure 36:
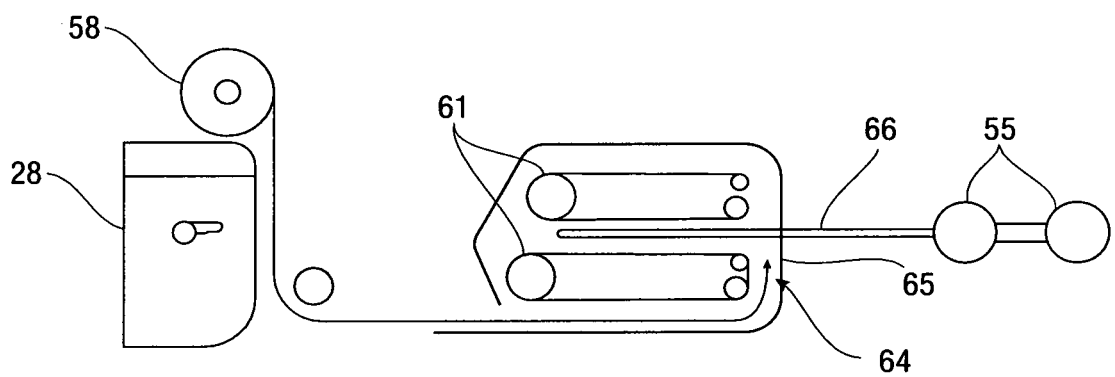
FIG. 36 shows a partial side plan view of an aspect of the smart toilet system of the present disclosure.

In FIG. 29, the view is of the ORG 20, opened up and from above, showing the toilet user's wiper system 52, the motorized hygiene wiper 53, with the cylindrical balls 55 extended into the toilet bowl 30 below the user. The tissue roll feeder 58 feeds toilet paper 64 through the toilet-paper-feeder port 63, where it is picked up by a plurality of conveyor belts 59, one on each edge of the top of the toilet paper 64, which is advantageously horizontal as it enters the toilet-paper-feeder port 63. Each of the plurality of conveyor belts 59 is driven by a plurality of conveyor wheels 61. A first conveyor belt 59a and a second conveyor belt 59b contact the toilet paper 64 at the outside edges of the toilet paper 64, on top of the toilet paper 64 and with the toilet paper 64 pressed against the plurality of conveyor belts 59 by a pressure plate 65 within the ORG 20, such that the plurality of conveyor belts 59 contacts the plurality of toilet paper 64. In some aspects of the present disclosure, as shown in FIG. 34 and FIG. 36, the plurality of conveyor belts 59 may comprise three such conveyor belts: a first conveyor belt 59a and a third conveyor belt 59c stacked above and below each other, and a second conveyor belt 59b; this arrangement allows the motorized hygiene wiper 53 to operably extend and retract, driven and operated in the space between the first conveyor belt 59a and the third conveyor belt 59c. The first conveyor belt 59a and the third conveyor belt 59c may be on the left side of the ORG 20, and the second conveyor belt 59b on the right side of the ORG 20, or vice-versa, as will be apparent to one of skill in the art. The pressure plate 65 may wrap around any extent of the plurality of conveyor belts 59. The plurality of conveyor belts 59 rotate, as shown in FIG. 30 where each of the first conveyor belt 59a and the second conveyor belt 59b are shown rotated 90° about their long axes, to illustrate their rotation, in the top plan view of FIG. 30. As the plurality of conveyor belts 59 rotate, then wrap one or more layers of toilet paper 64 around themselves, with the toilet paper 64 contacted only at the edges of the first conveyor belt 59a and of the second conveyor belt 59b; e.g. with the left edge of the toilet paper 64 contacted by the first conveyor belt 59a and the third conveyor belt 59c, and the right edge of the toilet paper 64 contacted by the second conveyor belt 59b. The plurality of conveyor belts 59 are disposed with the cylindrical balls 55 between them, such that the plurality of conveyor belts 59 wrap the toilet paper 64 around the cylindrical balls 55.

When the cylindrical balls 55 have a quantity of toilet paper 64 wrapped around them, the cylindrical balls 55 are then extended out of the ORG 20 by the motorized hygiene wiper 53, as shown in FIG. 30 and FIG. 31A and FIG. 31B. The cylindrical balls 55 are thus extended into a space of the toilet bowl 30, below the user seated on the smart toilet system 10 and toilet seat 26, taking with them (the cylindrical balls 55) the toilet paper 64 that has been wrapped around them. The cylindrical balls 55 may enter the toilet bowl 30 space extending horizontally or approximately horizontally from the motorized hygiene wiper 53 and an extensible arm 66. Upon entry into the toilet bowl 30 space, the cylindrical balls 55 may advantageously be rotated up from the horizontal to make contact with the user. The cylindrical balls 55 may then be rotated by the motorized hygiene wiper 53, with a connection enabling rotation via the extensible arm 66 as shown in FIG. 31A and FIG. 31B, such that the cylindrical balls 55 can effectively wipe the user of waste. After wiping the user of waste, the cylindrical balls 55 may be rotated down from a horizontal level, around the extensible arm 66 of the motorized hygiene wiper 53, whereupon the cylindrical balls 55 can be collapsed or reduced in volume, such as by an accordion or folding action. By so collapsing, the cylindrical balls 55 may drop the toilet paper 64 that has been soiled into the toilet bowl 30. Thereupon, the cylindrical balls 55 may rotate back to the horizontal or approximately horizontal, and be retracted by the motorized hygiene wiper 53 and the extensible arm 66 into the ORG 20.

Referring now to FIG. 3, the plumbing system 50 is configured to supply water to the smart toilet system 10. In one embodiment, the plumbing system 50 may be electronically controlled. The plumbing system 50 is connected to provide fluid (i.e., water) to the toilet bowl 30 and toilet tank 28 to provide flushing capabilities. The plumbing system 50 may provide fluid (e.g., water) to the rear bidet sprayer head 40.

As depicted in FIG. 2A, FIG. 3, and FIGS. 7-9, the rear bidet sprayer head 40 associated with the ORG 20 is connected to the plumbing system 50 through materials used in the art. The fluid levels of the rear bidet sprayer head 40 can be adjusted manually or electrically. The fluid of the rear bidet sprayer head 40 may be cold, room temperature, or heated. Further, the fluid of the rear bidet sprayer head 40 may travel through the vessel 51 with a capability of warming up the fluid as depicted in FIG. 3. With communication through the ORG 20 and the ORG processing-unit 300 by automatic functionalities or by remote control.

Referring to FIG. 22, an automatic flush mechanism comprising a toilet handle 202, and a switch 204 that is attached onto the toilet tank 28 by standard means as used in the art (e.g., screws, bolts, and nuts). The switch 204 may be electronic or mechanical, or other type of switch as known in the art, such that the switch 204 may actuate the rodded handle 203, and may be activated wired or wirelessly. The toilet handle 202 is connected to a rodded handle 203 as used in the art. The end of the rodded handle 203 opposite the toilet handle 202 is attached to a pull chain 206 that is attached to and is capable of pulling up a flapper 208. The switch 204 communicates with components supported by or enclosed by the ORG 20 to allow automatic flushing capabilities.

Referring to FIG. 10A and FIG. 10B, the electrical components supported by or enclosed within the ORG 20 (the motion sensors 44, lighting elements 56, and body weight sensors 46), the toilet seat (impedance photoplethysmography sensors 36), and toilet seat cover 24 (infrared lights 32, impedance photoplethysmography sensors 36 and the glucose monitor 33) may be connected to the control box 160 by electrical connection for power.

In an embodiment, as depicted in FIG. 16B, the wires of the control box 160 are situated within the VET 18. The wires of the control box 160 may pass from the VET 18 into the bathroom exhaust fan 12. As depicted in FIG. 16A, the wires of the control box 160 may be connected to the outlet or transformer within the bathroom exhaust fan 12. In another embodiment, the control box 160 may communicate with the ORG 20 wirelessly to provide input or power. Electrical power of the control box 160 may be provided through wireless means as known in the art (e.g., wireless power transmission).

Referring to FIG. 19 and FIG. 20, the control box 160 contains DC or AC power connections 86. The DC or AC power connections 86 are covered within the shell of the VET 18 as depicted in FIG. 18. The DC or AC power connections 86 are capable of connecting with the electrical components of the ORG 20 (the motion sensors 44, lighting elements 56, and body weight sensors 46, impedance photoplethysmography sensors 36), the toilet seat cover 24 (the infrared lights 32), and electrically motorized in-apparatus fans 14.

In an embodiment, as depicted in FIG. 18, the control box 160 of FIG. 1, FIG. 2B, and FIG. 3 may be capable of housing the remote control 84 of the smart toilet system 10. FIG. 21 provides possible examples of the interface of the remote control 84. The remote control 84 may be charged wirelessly or by USB connection to the control box 160. The remote control 84 has the capability of turning on and off the electrical components of the ORG (the motion sensors 44, lighting elements 56, and body weight sensors 46, and impedance photoplethysmography sensors 36), the toilet seat cover 24 (the infrared lights 32), and electrically motorized in-apparatus fans 14. Data collected from the body weight sensors 46 and impedance photoplethysmography sensors 36 may be collected onto the remote control 84, the control box 160, or sent to a cloud-based server.

Referring now to FIG. 28, which is a sample of the several optionally requested features, in a block diagram illustrating the electrical components of the smart toilet system 10 is shown, according to an exemplary embodiment of the smart toilet system 10 is shown to include a processing circuit 140 including a processor 142 and a memory 144. The smart toilet system 10 is further shown to include a set of communications electronics 120, a remote receiver 136, a PSU 146, a lighting element 148, and the optical sensor waste analyzer 57.

Still referring to FIG. 28, the processing circuit 140 is shown to include a processor 142 and memory 144. Processor 142 may be implemented as a general-purpose processor, an application specific integrated circuit (ASIC), one or more field programmable gate arrays (FPGAs), a CPU, a GPU, a group of processing components, or other suitable electronic processing components. Memory 144 may include one or more devices (e.g., RAM, ROM, Flash memory, hard disk storage, etc.) for storing data and/or computer code for completing and/or facilitating the various processes, layers, and modules described in the present disclosure. Memory 144 may include volatile memory or non-volatile memory. Memory 144 may include database components, object code components, script components, or any other type of information structure for supporting the various activities and information structures described in the present disclosure. For example, memory 144 may include instructions for interpreting (e.g., via processor 142) the various inputs received from communications electronics, remote control 84 and a control panel. Memory 144 may further include instructions for activating lighting elements 56, causing sound to be emitted from a speaker, or for initiating a flushing, sanitizing, or cleaning process. Still referring to FIG. 28, the smart toilet system 10 may further include one or more communications electronics. Communications electronics may include a USB connection, a memory card reader, an auxiliary input, a radio receiver, a wireless networking device, a wired networking device, or a remote control 84. Communications electronics may allow the fixture, the smart toilet system 10 to communicate with one or more mobile data sources such as a USB memory device, a memory card, a portable hard drive, or a mobile media device (e.g., a portable audio playback device). Communications electronics may also allow smart toilet system 10 to communicate with a wireless networking device (e.g., a wireless router, cell phone, wireless enabled computer, laptop, tablet, or other wireless device) or a wired networking device (e.g., via an Ethernet cable, a SATA cable, USB cable, or other physical data connection). Any of the foregoing wireless networking devices may be used to store, log, track, and/or share information related to diagnosis or treatment of medical conditions or diseases, including but not limited to COVID-19 and comorbidities for COVID-19.

In some embodiments, communications electronics enable smart toilet system 10 to send or receive data such as electronic media (e.g., audio or video files, audio or video streams, pictures, etc.), configuration information (e.g., system settings, user preferences, etc.), or operating commands (e.g., initiating the flushing process, activating infrared lights 32, activating lighting elements 56, or emitting sound from speaker). Communications electronics may enable the smart toilet system 10 to receive updates such as improved operating system software, updated firmware, user interface upgrades, or other product alterations or modifications. In addition to the devices discussed herein, communications electronics may include one or more supplemental wired or wireless interfaces (e.g., jacks, antennas, transmitters, receivers, transceivers, wire terminals, Ethernet ports, Wi-Fi transceivers, or other near-field radio communications protocols, now known or later invented) for conducting data communications with local or remote devices or systems.

With reference to FIGS. 16B, 26, and 27, an alternative power source for the smart toilet system 10 may include a primary power source. In FIG. 28, some embodiments of the primary power source 141 is a wired connection to an external power source. For example, the primary power source 141 may be power from a standard residential or commercial power source (e.g., a 120V 60 Hz AC power supply). The smart toilet system 10 may be plugged into a standard residential electrical outlet which serves as primary power source 141, with a transformer and a Ground Fault Interceptor (GFI) safety ratings. The primary power source 141 may be another source of power, now known or later invented.

The smart toilet system 10 may further include a battery pack. The battery pack may be inserted and/or removed from the smart toilet system 10. The battery pack may contain one or more batteries and may arrange the batteries in series, in parallel, or in both configurations. The battery pack may function as a voltage stack, allowing multiple batteries to be combined into a larger battery with a greater terminal voltage. The battery pack may serve as a backup power supply for the smart toilet system 10. The backup power supply may allow normal operation of smart toilet system 10 to continue in the event of a power failure.

The smart toilet system 10 may further include a power supply unit, abbreviated herein as PSU 146. The PSU 146 may receive power from a power source (e.g., the primary power source 141, or from solar power, and/or from a battery pack). In some embodiments, the PSU 146 transforms (e.g., the voltage of the power source), converts (e.g., from alternating current to direct current), or otherwise alters the power from a power source. The PSU 146 may provide power to the components of the smart toilet system 10. In some embodiments, the PSU 146 functions autonomously. In other embodiments, the processing circuit 140 may control the PSU 146. In other embodiments, the PSU 146 performs other functions, such as providing short circuit protection, overpower protection, overvoltage protection, undervoltage protection, overcurrent protection, over temperature protection, or other support to the components of the smart toilet system 10.

In some embodiments, the PSU 146 includes a power source switch. The PSU 146 may use the power source switch to switch between the primary power source and the battery pack to power the components of the smart toilet system 10. In some embodiments, the PSU 146 and/or the power switch automatically switches between the primary power source and the battery pack. For example, upon detecting a power outage (e.g., no power is available from the primary power source), the PSU 146 and/or the power source switch may automatically begin drawing power from the battery pack. In some embodiments, when the power outage ends (e.g., power is available from the primary power source again), the PSU 146 and/or the power source switch automatically switches to drawing power from the primary power source. In other embodiments, the PSU 146 and/or the power source switch may be controlled by the processing circuit. In some embodiments, the PSU 146 and/or the power switch allow for the recharging of the battery pack. In further embodiments, a depleted battery pack may be switch for a charged battery pack.

Figure 32:
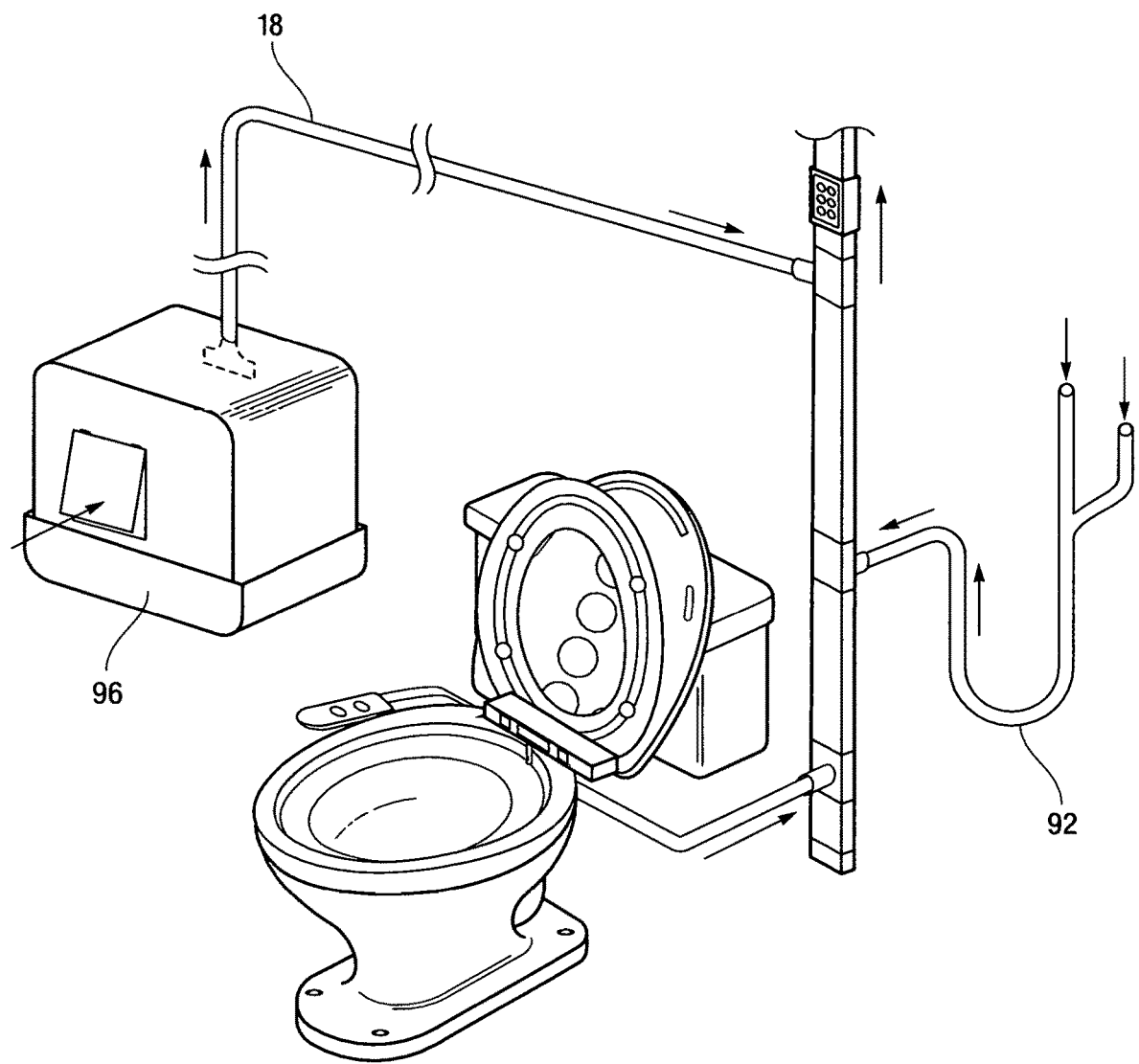
FIG. 32 shows a perspective view of an embodiment of the smart toilet system of the present disclosure.
Figure 33:
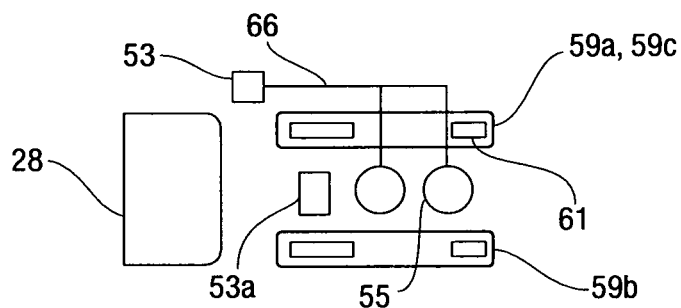
FIG. 33 shows a partial top plan view of an aspect of the smart toilet system of the present disclosure.

As shown in FIG. 28 and FIG. 32, the smart toilet system 10 may be configured to safely and more hygienically include the VET arm 62, a cat litter box odor vacuum 94, a cat litter box odor vacuum motion sensor 96, and a smoke device 92. Within whole health standards and the Fire Codes, medical marijuana, and comfort animals, according to Social Determinants Of Health (SDOH), these benefits are easily achieved with the advent of the VET arm 62, the cat litter box odor vacuum motion sensor 96, and the smoke device 92 connect to the ORG 20 through the plumbing connection tee tubing 70 of the VET 18 as depicted in FIG. 15 and FIG. 32. The foregoing, or a plurality of thereof, are supported by the ORG 20 to provide data input received from a user of the smart toilet system 10; the data collected from any of the sensors disclosed in the present disclosure are transmitted to the control box 160, announced via speaker, or collected in an external server (e.g., an. external cloud server). The cat litter box odor vacuum 94 and smoke device 92 are activated or deactivated by, i.e. turned on or off through, motion sensors 44, and/or cat litter box odor vacuum motion sensor 96, and/or by remote control access either by a remote control 84. The remote control 84 communicates with the control box 160, wherein the control box 160 provides the input to turn on or off the cat litter box odor vacuum 94 or smoke device 92. The cat litter box odor vacuum motion sensor 96 for the cat litter box odor vacuum 94 and the switch for smoke device 92 are supported by the ORG 20, wherein ORG 20 receives information for turning on or off to the cat litter box odor vacuum 94 or smoke device 92 from the control box 160 or from the remote control 84. The ORG 20, the VET 18, and the cat litter box odor vacuum 94 may be operably interconnected as a vacuuming system 114, as described above.

Certain aspects of the present invention were described above. From the foregoing it will be seen that this invention is one well adapted to attain all the ends and objects set forth above, together with other advantages, are obvious and inherent to the system and method of the present invention. It will be understood that certain features and sub-combinations are of utility and may be employed without reference to other features and sub-combinations. It is expressly noted that the present invention is not limited to those aspects described above, but rather the intention is that additions and modifications to what was expressly described herein are also included within the scope of the invention. Moreover, it is to be understood that the features of the various aspects described herein are not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

Accordingly, what is claimed is:

1. A smart toilet system that assists in hygiene, configured to monitor, measure and analyze, data of a user comprising a toilet seat, a toilet seat cover, and a control center (ORG), the ORG comprising: a processor and a memory component configured to receive and store data from a plurality of sensors; wherein the plurality of sensors comprise body mass index (BMI) sensors, electrocardiogram (ECG) sensors, weight sensors, and a plurality of motion sensors; and wherein the plurality of sensors and one or more lighting elements are printed onto the toilet seat or the toilet seat cover with printed electronics and infrared light treatment; a vacuum system component configured to remove odor by sucking air and odor through a plurality of vacuum system front odor openings and out of a plurality of vacuum system rear odor openings: a rear bidet sprayer head component, a front bidet sprayer head component a toilet paper wiper system component comprising a tissue roll feeder, a plurality of conveyor belts, a plurality of toilet paper, a plurality of cylindrical balls, a motorized hygiene wiper, and an extensible arm, the toilet paper system configured to clean the user, and a user arm controller that is electrically connected with the processor and is configured to receive input from the user; wherein the processor receives and processes the user input and transmits a signal to a display device or an audio sound device and wherein the user input is processed to control the ORG components.

2. The smart toilet system of claim 1, wherein the processor comprises a processing circuit.

3. The smart toilet system of claim 1, wherein the ORG is configured to house or support the plurality of sensors, the one or more lighting elements, a plurality of photoplethysmography sensors, a glucose monitor, electrodes, and a plurality of infrared lights.

4. The smart toilet system of claim 3, wherein data from the motions sensors are used to activate or deactivate the plurality of sensors, the one or more lighting elements, the plurality of impedance photoplethysmography sensors, the glucose monitor, and the plurality of infrared lights.

5. The smart toilet system of claim 3, wherein the plurality of motion sensors are located at the front of and at a plurality of tips of the ORG.

6. The smart toilet system of claim 3, wherein the plurality of infrared lights; the glucose monitor and the plurality of impedance photoplethysmography sensors are placed under or on an upper surface of the toilet seat; and are disposed on the toilet seat cover.

7. The smart toilet system of claim 1, further comprising a vacuum exhaust tubing (VET) configured to be connected with the plurality of vacuum system rear odor openings to receive and expel the air and odor from the ORG.

8. The smart toilet system of claim 1, further comprising a vessel which is temperature-controlled and/or insulated, and is used to regulate water temperature from a water supply and/or supply water that is at a comfortable temperature to a rear bidet sprayer head component and/or to a front bidet sprayer head component.

9. The smart toilet system of claim 1, wherein the toilet seat further comprises a smooth flush finish fitted at a top surface of the toilet seat, and further comprising a plurality of impedance photoplethysmography sensors, a plurality of infrared lights, a plurality of electrodes, and a plurality of temperature sensors.

10. The smart toilet system of claim 9, wherein the plurality of electrodes transmits sound waves back and forth by electrical echo signals in an upward direction from the toilet seat having a smooth flush finish, wherein the plurality of electrodes ultrasonically configured to measure and identify the user by communicating data with the processor.

11. The smart toilet system of claim 1, wherein an intense pulse light is disposed at or approximately at a top and center position of the toilet seat cover.

12. The smart toilet system of claim 1, further comprising an electronic blood pressure monitoring device having a cuff and a defibrillator attached thereto.

13. The smart toilet system of claim 1, wherein the vacuuming system further comprising a fan deodorizer and a vacuum exhaust tubing (VET) configured to connect to a bathroom exhaust fan.

14. The smart toilet system of claim 1, further comprising an automatic flush mechanism comprising a toilet handle and a switch, wherein the switch is attached to a toilet tank, and wherein the switch actuates a rodded handle.

15. The smart toilet system of claim 1, wherein the plurality of conveyor belts contacts the plurality of toilet paper, and the plurality of conveyor belts rotate to wrap one or more layers of toilet paper around the plurality of conveyor belts and around the plurality of cylindrical balls, and wherein the motorized hygiene wiper extends the plurality of cylindrical balls out of the ORG and into a space of a toilet bowl below the user; the plurality of cylindrical balls are rotated by the motorized hygiene wiper and the extensible arm to wipe the user of waste; after which, the cylindrical balls are rotated down from a horizontal level, whereupon the cylindrical balls are collapsed or reduced in volume; after which the cylindrical balls are rotated back to the horizontal or approximately horizontal, and are retracted by the motorized hygiene wiper and the extensible arm into the ORG.

16. The smart toilet system of claim 1, further comprising a vacuum exhaust tubing (VET) configured to be connected with the rear of ORG and/or a cat litter box odor vacuum; and wherein the vacuuming system is activated or deactivated by a cat litter box odor vacuum motion sensor, and/or a remote control, and/or the plurality of motion sensors.

17. The smart toilet system of claim 1, further comprising a vacuum exhaust tubing (VET) configured to be operably connected to the rear of ORG and/or a smoking device vacuum; and wherein the vacuuming system is activated or deactivated by a motion sensor, and/or a remote control, and/or the plurality of motion sensors.

18. The smart toilet system of claim 1, wherein the processor implements artificial intelligence (AI) and machine learning (ML) to process received data and health information from the plurality of sensors.

19. The smart toilet system of claim 1, wherein the ORG further comprises an optical sensor waste analyzer configured to scan and analyze one or more of urine and/or fecal matter; and wherein the optical sensor waste analyzer is disposed in the ORG housing, in the toilet seat.

20. The smart toilet system of claim 1, wherein the smart toilet system is configured to communicate with a smart mirror or a remote control, wherein the remote control and smart mirror include one or more software application configured to store, log, track and share information.

* * * * *